US010161748B2

(12) United States Patent
Arai

(10) Patent No.: US 10,161,748 B2
(45) Date of Patent: Dec. 25, 2018

(54) ULTRASONIC MEASUREMENT APPARATUS AND ULTRASONIC PROBE

(71) Applicant: Seiko Epson Corporation, Tokyo (JP)

(72) Inventor: Yoshio Arai, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/685,340

(22) Filed: Aug. 24, 2017

(65) Prior Publication Data

US 2018/0058845 A1    Mar. 1, 2018

(30) Foreign Application Priority Data

Aug. 31, 2016  (JP) ................................ 2016-168967

(51) Int. Cl.
*G01B 17/04* (2006.01)
*A61B 8/00* (2006.01)
*G01B 17/00* (2006.01)

(52) U.S. Cl.
CPC ................ *G01B 17/04* (2013.01); *A61B 8/46* (2013.01); *G01B 17/00* (2013.01)

(58) Field of Classification Search
CPC .......... G01B 9/02; G01B 17/00; G01B 17/04; A61B 8/46; A61B 8/00
See application file for complete search history.

(56) References Cited

U.S. PATENT DOCUMENTS

| 6,248,069 | B1* | 6/2001 | Liu ........................ A61B 8/00 |
| | | | 365/151 |
| 6,609,425 | B2* | 8/2003 | Ogawa ................ A61B 5/0097 |
| | | | 600/447 |
| 6,783,494 | B2* | 8/2004 | Ogawa ................ A61B 5/0097 |
| | | | 600/437 |
| 6,890,301 | B2* | 5/2005 | Jago ................... G01S 7/52025 |
| | | | 600/437 |
| 6,999,685 | B1* | 2/2006 | Kawase ............... A61B 5/0031 |
| | | | 398/129 |
| 7,367,945 | B2 | 5/2008 | Dasgupta et al. |

(Continued)

FOREIGN PATENT DOCUMENTS

| JP | 2005-279274 A | 10/2005 |
| JP | 2007-125225 A | 5/2007 |

(Continued)

*Primary Examiner* — Jewel V Dowtin
(74) *Attorney, Agent, or Firm* — Harness, Dickey & Pierce, P.L.C.

(57) ABSTRACT

An ultrasonic measurement apparatus includes: a first phasing addition circuit that receives electric signals output from a plurality of reception ultrasonic elements, shifts the plurality of electric signals in a time axis direction to combine the plurality of electric signals, and outputs a composite signal; a second electro-optical conversion unit and a second light emitting unit that receive the composite signal, convert the composite signal into an optical signal, and output the optical signal; an optical cable through which the optical signal is transmitted; and a second light receiving unit and a second photoelectric conversion unit that receive the optical signal and converts the optical signal into an electric signal. The second light emitting unit outputs the optical signal after the first phasing addition circuit outputs the composite signal.

10 Claims, 10 Drawing Sheets

(56) References Cited

U.S. PATENT DOCUMENTS

| | | | |
|---|---|---|---|
| 7,525,661 B2 * | 4/2009 | Mandelis | G01B 21/085 356/237.1 |
| 7,615,009 B2 * | 11/2009 | Koste | A61B 8/14 600/443 |
| 9,170,660 B2 | 10/2015 | Takeda | |
| 2005/0215894 A1 | 9/2005 | Dasgupta et al. | |
| 2007/0016044 A1 * | 1/2007 | Blalock | G01S 7/52017 600/443 |
| 2007/0167816 A1 | 7/2007 | Koste et al. | |
| 2010/0106297 A1 | 4/2010 | Inazumi et al. | |
| 2010/0121489 A1 | 5/2010 | Inazumi et al. | |
| 2012/0299878 A1 | 11/2012 | Takeda | |

FOREIGN PATENT DOCUMENTS

| | | |
|---|---|---|
| JP | 2010-100421 A | 5/2010 |
| JP | 2010-115723 A | 5/2010 |
| JP | 2012-209747 A | 10/2012 |
| JP | 2012-243201 A | 12/2012 |
| JP | 2012-243202 A | 12/2012 |
| WO | WO-1998-051025 A1 | 11/1998 |

\* cited by examiner

ULTRASONIC MEASUREMENT APPARATUS AND ULTRASONIC PROBE

BACKGROUND

1. Technical Field

The present invention relates to an ultrasonic measurement apparatus and an ultrasonic probe.

2. Related Art

There is known an ultrasonic measurement apparatus that emits ultrasonic waves toward an object and receives reflected waves from the interfaces having different acoustic impedances inside the object. The ultrasonic measurement apparatus is used, for example, to examine the inside of a human body that is a subject.

Such an ultrasonic measurement apparatus is disclosed in JP-A-2007-125225. The ultrasonic measurement apparatus includes a main body and an ultrasonic probe. In the ultrasonic probe, an ultrasonic element emits ultrasonic waves to the object and receives reflected waves that are reflected from the object. Then, the ultrasonic element converts the waveform of each reflected wave into an electric signal. Then, the ultrasonic probe outputs the electric signal indicating the reflected wave to the main body. In the main body, a calculation using the electric signal is performed to form and display an ultrasonic image.

In a case where a number of ultrasonic elements are provided in the ultrasonic probe, the amount of information transmitted to the main body by the ultrasonic probe increases in proportion to the number of ultrasonic elements. In order to transmit a large amount of information from the ultrasonic probe to the main body, optical communication is adopted. The ultrasonic probe and the main body are connected to each other by an optical cable.

In order to increase the resolution of the ultrasonic image, it is necessary to increase the number of ultrasonic elements. Also in the case of displaying an ultrasonic stereoscopic image by arranging the ultrasonic elements in a two-dimensional manner, it is necessary to increase the number of ultrasonic elements. In this case, since the amount of information transmitted through the optical cable increases, it is necessary to thicken the optical cable.

The operator grips the ultrasonic probe by hand to operate it. In this case, if the optical cable is thick, it is difficult for the operator to bend the optical cable. In this case, since it is difficult to tilt the ultrasonic probe freely, it is difficult to operate the ultrasonic probe. Therefore, there has been a demand for an ultrasonic measurement apparatus having a thin optical cable and good operability.

SUMMARY

An advantage of some aspects of the invention is to solve the problems described above and the invention can be implemented as the following forms or application examples.

Application Example 1

An ultrasonic measurement apparatus according to this application example includes: a combining processing circuit that receives electric signals output from a plurality of ultrasonic elements, shifts the plurality of electric signals in a time axis direction to combine the plurality of electric signals, and outputs a composite signal; an electro-optical conversion unit that receives the composite signal, converts the composite signal into an optical signal, and outputs the optical signal; an optical fiber through which the optical signal is transmitted; and a photoelectric conversion unit that receives the optical signal and converts the optical signal into an electric signal. The electro-optical conversion unit outputs the optical signal after the combining processing circuit outputs the composite signal.

According to this application example, the ultrasonic measurement apparatus includes the combining processing circuit, the electro-optical conversion unit, the optical fiber, and the photoelectric conversion unit. The combining processing circuit receives the electric signals output from the plurality of ultrasonic elements. Then, the combining processing circuit shifts the plurality of electric signals in the time axis direction to combine the plurality of electric signals. Then, the composite signal is output. The electro-optical conversion unit receives the composite signal. Then, the electro-optical conversion unit converts the composite signal into an optical signal, and outputs the optical signal to the optical fiber. The optical signal is transmitted through the optical fiber. The photoelectric conversion unit receives the optical signal and converts the optical signal into an electric signal.

The ultrasonic waves emitted from the ultrasonic elements are reflected by an object to be measured, and the reflected waves are received by the ultrasonic elements. In this case, the ultrasonic element, which is far from the reflection place of the reflected wave, receives the reflected wave later than the ultrasonic element close to the reflection place of the reflected wave. Therefore, the composite signal obtained by combining the electric signals, which are received and output by the respective ultrasonic elements, by shifting the electric signals in the time axis direction is a signal that includes distance information between the ultrasonic element and the reflection place of the ultrasonic wave and that has a high signal strength compared with noise.

Since each of the ultrasonic elements outputs an electric signal, the number of electric signals output from the group of ultrasonic elements increases as the number of ultrasonic elements increases. Then, the combining processing circuit combines the plurality of electric signals. In this manner, it is possible to reduce the amount of electric signals transmitted through the optical fiber. Then, the electro-optical conversion unit converts the composite signal into an optical signal, and transmits the optical signal through the optical fiber. The photoelectric conversion unit receives the optical signal and converts the optical signal into an electric signal. In this manner, it is possible to utilize the composite signal obtained by combining the electric signals output from the respective ultrasonic elements.

When the electric signal output from the ultrasonic element is transmitted as it is, the number of wirings for transmission is increased. For the wiring of the electric signal, metal is used. Therefore, if the number of wirings is large, it is difficult for the wirings to bend. For this reason, the operability is lowered. In the ultrasonic measurement apparatus according to this application example, instead of the electric signal, the optical signal is transmitted through the optical fiber. Since a thin wire, such as a glass wire or a transparent resin wire, can be used for the optical fiber, the optical fiber can be made thin so as to be able to bend. Since the combining processing circuit combines the electric signals before the electro-optical conversion unit outputs the optical signal, it is possible to reduce the amount of optical signals to be transmitted. As a result, since the optical fiber can be made thin so as to be able to bend, the ultrasonic measurement apparatus having good operability can be obtained.

Application Example 2

In the ultrasonic measurement apparatus according to the application example, the electric signal output from each of the ultrasonic elements may be an analog signal, and the ultrasonic measurement apparatus may include an A/D conversion unit, which converts the analog signal into a digital signal and outputs the digital signal, and a serial conversion unit, which serializes the digital signal to output a serial signal, the combining processing circuit may output the composite signal after the A/D conversion unit outputs the digital signal and the serial conversion unit may output the serial signal after the combining processing circuit outputs the composite signal.

According to this application example, the electric signal output from each of the ultrasonic elements is an analog signal. The ultrasonic measurement apparatus includes the A/D conversion unit and the serial conversion unit. The A/D conversion unit converts the analog signal into a digital signal. By using a digital arithmetic device, an advanced calculation is performed on the digital signal. As a result, it is possible to form an ultrasonic cross-sectional image. After the A/D conversion unit outputs the digital signal, the combining processing circuit outputs the composite signal. Since the combining processing circuit can perform processing using a digital signal, the processing can be performed more easily compared with a case in which an analog signal is used. After the combining processing circuit outputs the composite signal, the serial conversion unit serializes the digital signal to output a serial signal. Due to the serial signal, it is possible to reduce the number of signal wirings compared with a case of the parallel signal. As a result, since the optical fiber can be made easy to bend, the ultrasonic measurement apparatus having good operability can be obtained.

Application Example 3

An ultrasonic measurement apparatus according to this application example includes: a multiplexing processing unit that receives electric signals output from a plurality of ultrasonic elements, time-division multiplexes the plurality of electric signals, and outputs a multiplexed signal obtained by the time-division multiplexing; an electro-optical conversion unit that receives the multiplexed signal and converts the multiplexed signal into an optical signal; an optical fiber through which the optical signal is transmitted; and a photoelectric conversion unit that receives the optical signal and converts the optical signal into an electric signal. The electro-optical conversion unit outputs the optical signal after the multiplexing processing unit outputs the multiplexed signal.

According to this application example, the ultrasonic measurement apparatus includes the multiplexing processing unit, the electro-optical conversion unit, the optical fiber, and the photoelectric conversion unit. The multiplexing processing unit receives the electric signals output from the plurality of ultrasonic elements. Then, the multiplexing processing unit time-division multiplexes the electric signals. Then, the multiplexed signal obtained by the time-division multiplexing is output. The electro-optical conversion unit receives the multiplexed signal. Then, the multiplexed signal is converted into an optical signal. The optical signal is transmitted through the optical fiber. The photoelectric conversion unit receives the optical signal and converts the optical signal into a multiplexed signal in the form of an electric signal.

Since each of the ultrasonic elements outputs an electric signal, the number of electric signals output from the group of ultrasonic elements increases as the number of ultrasonic elements increases. Then, the multiplexing processing unit time-division multiplexes a plurality of electric signals. In this manner, it is possible to reduce the amount of electric signals transmitted through the optical fiber. Then, after the multiplexing processing unit outputs the multiplexed signal, the electro-optical conversion unit converts the multiplexed signal into an optical signal and transmits the optical signal through the optical fiber. The photoelectric conversion unit receives the optical signal and converts the optical signal into a multiplexed signal in the form of an electric signal. In this manner, it is possible to utilize the multiplexed signal obtained by time-division multiplexing the electric signals output from the respective ultrasonic elements.

When the electric signal output from the ultrasonic element is transmitted as it is, the number of wirings for transmission increases. For the wiring of the electric signal, metal is used. Therefore, if the number of wirings is large, it is difficult for the wirings to bend. For this reason, the operability is lowered. In the ultrasonic measurement apparatus according to this application example, instead of the electric signal, the optical signal is transmitted through the optical fiber. Since a thin wire, such as a glass wire or a transparent resin wire, can be used for the optical fiber, the optical fiber can be made thin so as to be able to bend. Since the multiplexing processing unit is disposed between the ultrasonic element and the electro-optical conversion unit and the multiplexing processing unit time-division multiplexes the electric signals, it is possible to reduce the amount of optical signals to be transmitted. As a result, since the optical fiber can be made thin so as to be able to bend, the ultrasonic measurement apparatus having good operability can be obtained.

Application Example 4

In the ultrasonic measurement apparatus according to the application example, the electric signal output from each of the ultrasonic elements may be an analog signal, and the ultrasonic measurement apparatus may include an A/D conversion unit, which converts the analog signal into a digital signal, and a serial conversion unit, which serializes the digital signal to output a serial signal.

According to this application example, the electric signal output from each of the ultrasonic elements is an analog signal. The ultrasonic measurement apparatus includes the A/D conversion unit and the serial conversion unit. The A/D conversion unit converts the analog signal into a digital signal. By using a digital arithmetic device, an advanced calculation is performed on the digital signal. As a result, it is possible to form an ultrasonic cross-sectional image. Then, the serial conversion unit serializes the digital signal to output a serial signal. Due to the serial signal, it is possible to reduce the number of signal wirings compared with a case of the parallel signal. As a result, since the optical fiber can be made easy to bend, the ultrasonic measurement apparatus having good operability can be obtained.

Application Example 5

The ultrasonic measurement apparatus according to the application example may further include a first circuit board on which the plurality of ultrasonic elements are provided and a second circuit board connected to the first circuit board by a wiring portion. The A/D conversion unit may be provided on the second circuit board.

According to this application example, the ultrasonic measurement apparatus includes the first circuit board and the second circuit board. The ultrasonic elements are provided on the first circuit board. The A/D conversion unit is provided on the second circuit board. The first circuit board and the second circuit board are separated from each other, but are connected to each other by the wiring portion. When the A/D conversion unit performs conversion processing at high speed, the A/D conversion unit generates heat. As a result, the temperature of the second circuit board rises.

The ultrasonic elements are provided on the first circuit board. When the temperature of the ultrasonic element rises, noise increases and accordingly the electric signal to be output fluctuates. As a result, the detection accuracy of the strength of the ultrasonic wave detected by the ultrasonic element is lowered. On the other hand, the first circuit board and the second circuit board are separated from each other, but are connected to each other by the wiring portion. Therefore, even if the temperature of the second circuit board rises, the temperature rise of the first circuit board is suppressed. As a result, it is possible to suppress a lowering in the detection accuracy of the strength of the ultrasonic wave detected by the ultrasonic element.

Application Example 6

In the ultrasonic measurement apparatus according to the application example, a second heat dissipation unit that dissipates heat of the second circuit board may be provided on the second circuit board.

According to this application example, the second circuit board includes the second heat dissipation unit, and the second heat dissipation unit dissipates the heat of the second circuit board. Therefore, it is possible to suppress the temperature rise of the second circuit board.

Application Example 7

In the ultrasonic measurement apparatus according to the application example, a first heat dissipation unit that dissipates heat of the first circuit board may be provided on the first circuit board.

According to this application example, the first circuit board includes the first heat dissipation unit, and the first heat dissipation unit dissipates the heat of the first circuit board. Therefore, it is possible to suppress the temperature rise of the first circuit board.

Application Example 8

In the ultrasonic measurement apparatus according to the application example, a heat insulation unit that blocks conductive heat may be provided between the first circuit board and the second circuit board.

According to this application example, the heat insulation unit is provided between the first circuit board and the second circuit board, and the heat insulation unit blocks conductive heat transferred from the second circuit board to the first circuit board. Therefore, it is possible to suppress the temperature of the first circuit board from rising even if the temperature of the second circuit board rises.

Application Example 9

The ultrasonic measurement apparatus according to the application example may further include: a multiplexing processing unit that receives the electric signals output from the plurality of ultrasonic elements, time-division multiplexes the plurality of electric signals, and outputs a multiplexed signal obtained by the time-division multiplexing; a first circuit board on which the plurality of ultrasonic elements are provided; and a second circuit board connected to the first circuit board by a wiring portion, and the multiplexing processing unit may be provided on the first circuit board, and the A/D conversion unit may be provided on the second circuit board.

According to this application example, the ultrasonic measurement apparatus includes the first circuit board and the second circuit board. The ultrasonic elements are provided on the first circuit board. The A/D conversion unit is provided on the second circuit board. The first circuit board and the second circuit board are separated from each other, but are connected to each other by the wiring portion. When the A/D conversion unit performs conversion processing at high speed, the A/D conversion unit generates heat. As a result, the temperature of the second circuit board rises.

The ultrasonic elements are provided on the first circuit board. When the temperature of the ultrasonic element rises, noise increases and accordingly the electric signal to be output fluctuates. As a result, the detection accuracy of the strength of the ultrasonic wave detected by the ultrasonic element is lowered. On the other hand, the first circuit board and the second circuit board are separated from each other, but are connected to each other by the wiring portion. Therefore, even if the temperature of the second circuit board rises, the temperature rise of the first circuit board is suppressed. As a result, it is possible to suppress a lowering in the detection accuracy of the strength of the ultrasonic wave detected by the ultrasonic element.

The multiplexing processing unit is provided on the first circuit board. Accordingly, since the amount of signals transmitted through the wiring portion can be reduced, the wiring portion can be made thin. As a result, it is possible to suppress the heat of the second circuit board from conducting to the first circuit board.

Application Example 10

An ultrasonic probe according to this application example includes: a combining processing circuit that receives electric signals output from a plurality of ultrasonic elements, shifts the plurality of electric signals in a time axis direction to combine the plurality of electric signals, and outputs a composite signal; and an electro-optical conversion unit that receives the composite signal and converts the composite signal into an optical signal transmitted through an optical fiber, and the electro-optical conversion unit may output the optical signal after the combining processing circuit outputs the composite signal.

According to this application example, the ultrasonic probe includes the combining processing circuit and the electro-optical conversion unit. The combining processing circuit receives the electric signals output from the plurality of ultrasonic elements. Then, the combining processing circuit shifts the plurality of electric signals in the time axis direction to combine the plurality of electric signals. Then, the combining processing circuit outputs the composite signal. The electro-optical conversion unit receives the composite signal. The composite signal is converted into an optical signal. The optical signal is transmitted through the optical fiber.

The ultrasonic waves emitted from the ultrasonic elements are reflected by an object to be measured, and the reflected waves are received by the ultrasonic elements. In this case, the ultrasonic element, which is far from the reflection place of the reflected wave, receives the reflected wave later than the ultrasonic element close to the reflection place of the reflected wave. Therefore, the composite signal obtained by combining the electric signals, which are received and output by the respective ultrasonic elements, by shifting the electric signals in the time axis direction is a signal that includes distance information between the ultrasonic element and the reflection place of the ultrasonic wave and that has a high signal strength compared with noise.

Since each of the ultrasonic elements outputs an electric signal, the number of electric signals output from the group of ultrasonic elements increases as the number of ultrasonic elements increases. Then, the combining processing circuit combines the plurality of electric signals. In this manner, it is possible to reduce the amount of electric signals transmitted through the optical fiber. Then, the electro-optical conversion unit converts the composite signal into an optical signal, and transmits the optical signal through the optical fiber.

When the electric signal output from the ultrasonic element is transmitted as it is, the number of wirings for transmission increases. For the wiring of the electric signal, metal is used. Therefore, if the number of wirings is large, it is difficult for the wirings to bend. For this reason, the operability is lowered. In the ultrasonic probe according to this application example, instead of the electric signal, the optical signal is transmitted through the optical fiber. Since a thin wire, such as a glass wire or a transparent resin wire, can be used for the optical fiber, the optical fiber can be made thin so as to be able to bend. Since the combining processing circuit combines the electric signals before the electro-optical conversion unit outputs the optical signal, it is possible to reduce the amount of optical signals to be transmitted. As a result, since the optical fiber can be made thin so as to be able to bend, the ultrasonic probe having good operability can be obtained.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments will be described with reference to the accompanying diagrams. In each diagram, the scale of each member is adjusted in order to have a recognizable size.

First Embodiment

Figure 1:
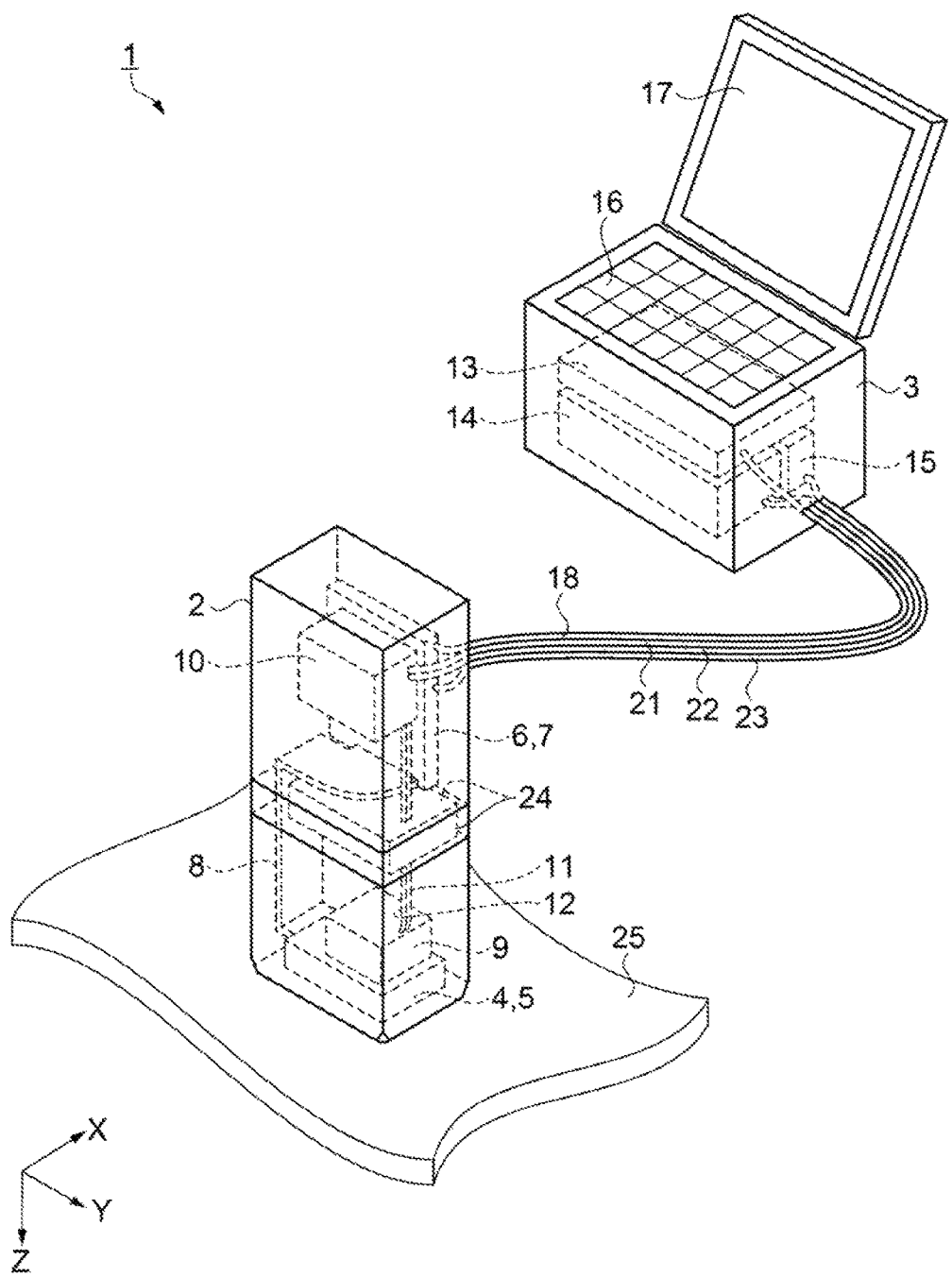
FIG. 1 is a schematic perspective view showing the configuration of an ultrasonic measurement apparatus according to a first embodiment.

In the present embodiment, characteristic examples of an ultrasonic probe and an ultrasonic measurement apparatus including the ultrasonic probe will be described with reference to the accompanying diagrams. An ultrasonic measurement apparatus according to the first embodiment will be described with reference to FIGS. 1 to 9. FIG. 1 is a schematic perspective view showing the configuration of the ultrasonic measurement apparatus. As shown in FIG. 1, an ultrasonic measurement apparatus 1 includes an ultrasonic probe 2 and a control device 3. The ultrasonic probe 2 has an approximately rectangular parallelepiped shape that is long in one direction, so that the operator easily grips the ultrasonic probe 2. The longitudinal direction of the ultrasonic probe 2 is defined as a Z direction. The surface of the ultrasonic probe 2 in the +Z direction is an approximately flat surface, and the planar shape is a rectangle. Directions in which two orthogonal sides of the planar shape extend are defined as X and Y directions. The longitudinal direction of the +Z-direction surface of the ultrasonic probe 2 is the Y direction.

An ultrasonic transducer device 4 is provided on the +Z-direction side of the ultrasonic probe 2. A first circuit board 5 is provided in the ultrasonic transducer device 4. Ultrasonic elements are arranged in a matrix in the ultrasonic transducer device 4, and each ultrasonic element emits an ultrasonic wave and receives a reflected wave. Then, the waveform of the reflected wave is converted into an electric signal, and the electric signal is output. Although the number of ultrasonic elements is not particularly limited, for example, an arrangement of 64 rows by 64 columns is adopted in the present embodiment. A circuit for supplying a drive signal to the ultrasonic element, a circuit for amplifying a signal output from the ultrasonic element, and the like are provided on the first circuit board 5.

On the surface of the ultrasonic probe 2 on the +Z-direction side, the ultrasonic transducer device 4 is exposed from the housing. An input and output control unit 6 is provided inside the ultrasonic probe 2, and a second circuit board 7 is provided in the input and output control unit 6. The first circuit board 5 and the second circuit board 7 are connected to each other by a wiring 8 as a wiring portion. A circuit for efficiently communicating with the control device 3 is provided on the second circuit board 7. The wiring 8 is a coaxial cable, and has a structure that suppresses the influence of electromagnetic wave noise.

A first heat dissipation unit 9 is provided on the first circuit board 5, and the first heat dissipation unit 9 dissipates the heat of the first circuit board 5. A second heat dissipation unit 10 is provided on the second circuit board 7, and the second heat dissipation unit 10 dissipates the heat of the second circuit board 7. The first heat dissipation unit 9 and the second heat dissipation unit 10 are connected to each other by a first refrigerant delivery pipe 11 and a first refrigerant discharge pipe 12.

The control device 3 is a device that receives a data signal output from the ultrasonic probe 2, performs a calculation using the data signal, and displays a result of the calculation. The control device 3 includes a control unit 13, a cooling unit 14, a power supply unit 15, an input unit 16, a display unit 17, and the like. The control unit 13 and the second circuit board 7 are connected to each other by an optical cable 18 as an optical fiber. The cooling unit 14 and the second heat dissipation unit 10 are connected to each other by a second refrigerant delivery pipe 21 and a second refrigerant discharge pipe 22. The power supply unit 15 and the second circuit board 7 are connected to each other by a power supply cable 23.

The control unit 13 includes a CPU, and the CPU performs various calculations or controls according to the program. Mainly, the control unit 13 controls ultrasonic waves output from the ultrasonic transducer device 4. An ultrasonic image is formed using the reflected wave signal received by the ultrasonic transducer device 4, and the ultrasonic image is displayed on the display unit 17.

The cooling unit 14 is a heat exchanger for cooling a refrigerant. The refrigerant is input from the second refrigerant discharge pipe 22, and the refrigerant is compressed to raise the temperature to facilitate heat dissipation. Then, the refrigerant is output to the second refrigerant delivery pipe 21. The refrigerant reaches the second heat dissipation unit 10. In the second heat dissipation unit 10, the refrigerant absorbs the heat of the second circuit board 7 and partly evaporates. The refrigerant reaches the first heat dissipation unit 9 through the first refrigerant delivery pipe 11. In the first heat dissipation unit 9, the refrigerant absorbs the heat of the first circuit board 5 and partly evaporates. The refrigerant returns to the cooling unit 14 through the first refrigerant discharge pipe 12 and the second refrigerant discharge pipe 22.

Since the refrigerant circulates as described above, the heat of the first circuit board 5 and the second circuit board 7 is absorbed by the refrigerant. Therefore, since the first circuit board 5 and the second circuit board 7 dissipate heat, it is possible to suppress a temperature rise.

In the ultrasonic probe 2, a heat insulation unit 24 for blocking conductive heat is provided between the first circuit board 5 and the second circuit board 7. The heat insulation unit 24 blocks conductive heat transferred from the second circuit board 7 to the first circuit board 5. Therefore, even if the temperature of the second circuit board 7 rises, it is possible to suppress the temperature rise of the first circuit board 5.

A number of ultrasonic elements are provided in the ultrasonic transducer device 4. Noise increases due to temperature rise in the ultrasonic element. By suppressing the temperature rise of the ultrasonic element using the first heat dissipation unit 9 and the second heat dissipation unit 10, it is possible to improve the S/N ratio of the signal output from the ultrasonic element.

The input unit 16 is a device, such as a keyboard or a mouse pad, and is a device for inputting the instruction contents given to the control device 3 by the operator. The display unit 17 is not particularly limited as long as it is possible to display the data signal as an image, and a liquid crystal display device or an organic light emitting diode (OLED) display device can be used. In the present embodiment, for example, an OLED is used for the display unit 17.

The ultrasonic probe 2 is used in a state of being pressed against the surface of a subject 25. The ultrasonic probe 2 emits ultrasonic waves from the ultrasonic transducer device 4 toward the subject 25. Then, the ultrasonic transducer device 4 receives reflected waves that are reflected from the inside of the subject 25. Since the time taken for reflection and return of the reflected wave differs depending on the reflected surface, it is possible to examine the internal structure of the subject 25 in a non-destructive manner by analyzing the return time of the reflected wave. The reflected wave signal received by the ultrasonic transducer device 4 is output to the input and output control unit 6. The input and output control unit 6 includes an analog-to-digital (A/D) conversion unit that performs A/D conversion, and converts the reflected wave signal into a digital format data signal. Then, the digital format data signal is transmitted from the input and output control unit 6 to the control unit 13 through the optical cable 18. The control unit 13 receives and analyzes the data signal of the reflected wave. Then, the control device 3 converts the internal structure of the subject 25 into an image, and displays the image on the display unit 17.

Figure 2:
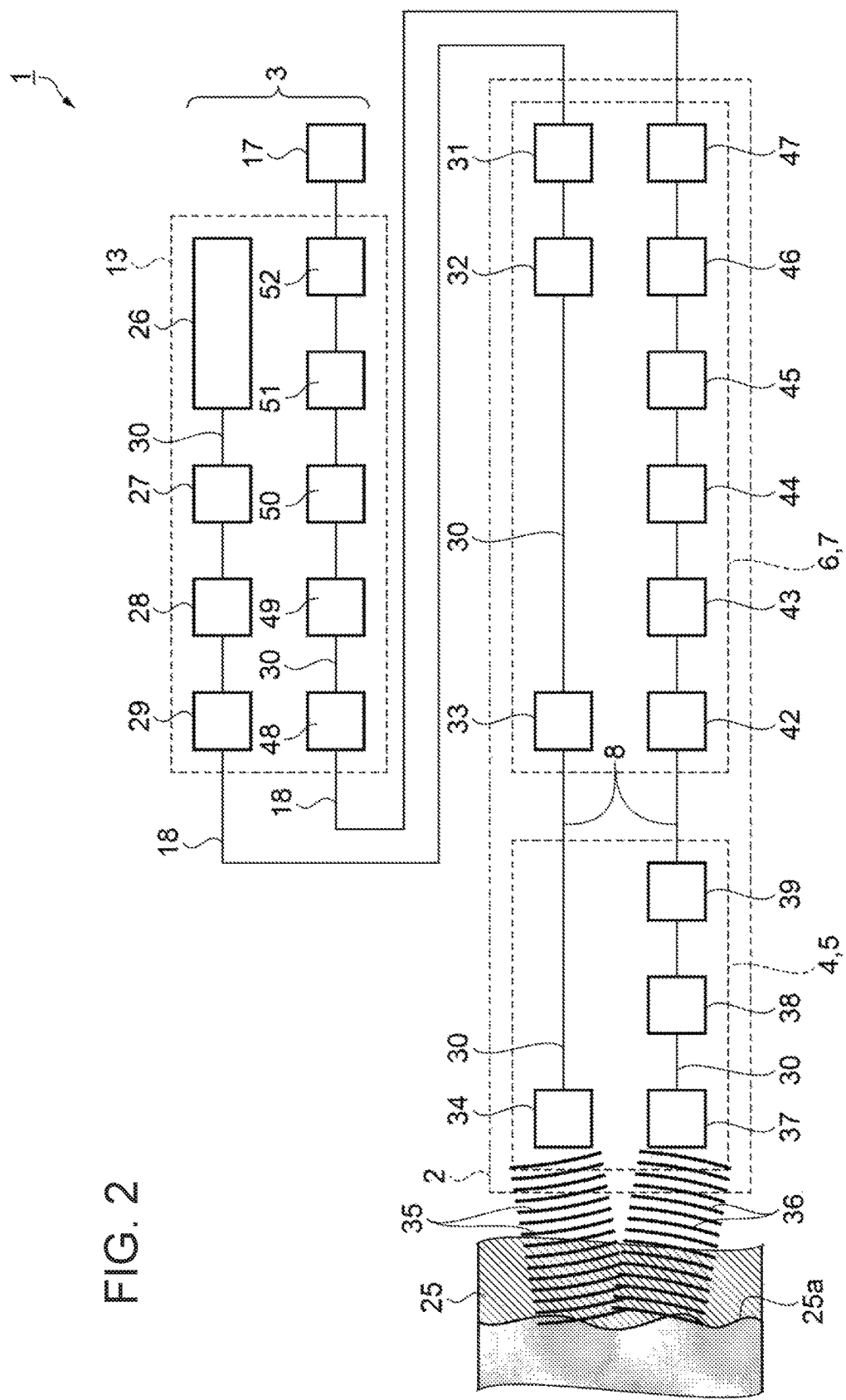
FIG. 2 is an electric block diagram of the ultrasonic measurement apparatus.

FIG. 2 is an electric block diagram of the ultrasonic measurement apparatus. As shown in FIG. 2, in the ultrasonic measurement apparatus 1, the control unit 13 is provided in the control device 3, and the first circuit board 5 and the second circuit board 7 are provided in the ultrasonic probe 2. The control unit 13 includes a transmission control unit 26, a waveform forming unit 27, a first electro-optical conversion unit 28, and a first light emitting unit 29. The transmission control unit 26, the waveform forming unit 27, the first electro-optical conversion unit 28, and the first light emitting unit 29 are connected to each other by a wiring 30 in this order.

The transmission control unit 26 controls the timing of an ultrasonic wave emitted from each ultrasonic element provided in the ultrasonic transducer device 4. The transmission control unit 26 outputs an instruction signal, which is for giving an instruction regarding the ultrasonic wave emission timing of each ultrasonic element, to the waveform forming unit 27. The waveform forming unit 27 receives the instruction signal and calculates a drive waveform signal for driving the ultrasonic element group. Then, the drive waveform signal is output to the first electro-optical conversion unit 28.

The first electro-optical conversion unit 28 is a light modulation driver for driving the first light emitting unit 29. The first light emitting unit 29 includes a light emitting element. The type of the light emitting element is not particularly limited, but it is possible to use a light emitting diode (LED), a laser diode (LD), or a vertical cavity surface emitting laser (VCSEL) manufactured with GaInAsP. In the present embodiment, for example, the VCSEL is used as the first light emitting unit 29. The first electro-optical conversion unit 28 receives the drive waveform signal, converts the drive waveform signal into a drive waveform for driving the first light emitting unit 29, and outputs the drive waveform to the first light emitting unit 29. The first light emitting unit 29 outputs an optical signal corresponding to the drive waveform signal. The optical cable 18 is connected to the first light emitting unit 29, and the optical signal is output to the optical cable 18. Although the wavelength of the optical signal is not particularly limited, it is preferable that the wavelength of the optical signal is 1540 nm that is the low loss wavelength band of the optical cable 18.

The optical signal is transmitted to the second circuit board 7 of the input and output control unit 6 through the optical cable 18. In the input and output control unit 6, a first light receiving unit 31, a first photoelectric conversion unit 32, and a pulse signal output unit 33 are formed on the second circuit board 7, and these are connected to each other by the wiring 30 in this order. The optical cable 18 is connected to the first light receiving unit 31. An element that converts light into an electric signal, such as a photodiode, is used as the first light receiving unit 31. The first light receiving unit 31 converts the optical signal into an electric signal, and outputs the electric signal to the first photoelectric conversion unit 32. The electric signal is a weak drive waveform signal.

A transimpedance amplifier (TIA) that is one type of an amplifier circuit is used as the first photoelectric conversion unit 32. The TIA is appropriately used since it is possible to increase the degree of amplification by extending the bandwidth. Then, the drive waveform signal amplified by the first photoelectric conversion unit 32 is output to the pulse signal output unit 33.

The pulse signal output unit 33 is a circuit called a pulser. The drive waveform signal is configured to include a signal indicating the timing of the drive waveform and a plurality of pulse signals indicating the waveform. The pulse signal output unit 33 forms a pulse waveform for driving the ultrasonic element using the plurality of pulse signals. Since the equivalent circuit of the ultrasonic element is formed by LRC (L: inductance R: resistance C: capacitance), the equivalent circuit can be normally driven even with a pulse waveform in which a drive waveform for driving an ultrasonic element is configured to include a plurality of rectangles. Then, the drive waveform output from the pulse signal output unit 33 is output to the ultrasonic transducer device 4. The drive waveform is transmitted through the wiring 8.

A plurality of transmission ultrasonic elements 34 for transmitting ultrasonic waves are provided on the first circuit board 5 of the ultrasonic transducer device 4. In order to make the diagram easy to see, one transmission ultrasonic element 34 is shown in the diagram. The transmission ultrasonic element 34 is a conversion element that receives an electric signal of a drive waveform and converts the electric signal into an ultrasonic signal. The transmission ultrasonic element 34 has an element shape suitable for transmitting an ultrasonic wave. Then, the transmission ultrasonic element 34 emits an ultrasonic wave 35 to the subject 25. The plurality of transmission ultrasonic elements 34 are arranged in a matrix. By adjusting the phase of the ultrasonic wave 35 transmitted from each transmission ultrasonic element 34, it is possible to increase the strength of the ultrasonic wave 35 in a specific place. The transmission control unit 26 controls the phase of the ultrasonic wave 35 transmitted from each transmission ultrasonic element 34. The transmission control unit 26 controls the place where the ultrasonic wave 35 emitted from the transmission ultrasonic element 34 converges.

Inside the subject 25, there is an interface 25a where the acoustic impedance changes. When the ultrasonic wave 35 converges on the interface 25a, a reflected wave 36 as an ultrasonic wave having a high strength is reflected from the interface 25a. Some of the reflected waves 36 are input to the ultrasonic transducer device 4.

In the ultrasonic transducer device 4, reception ultrasonic elements 37 as a plurality of ultrasonic elements, a plurality of multiplexing processing units 38, and a plurality of amplification units 39 are provided on the first circuit board 5, and these are connected to each other by the wiring 30 in this order. The plurality of reception ultrasonic elements 37 are arranged in a matrix. Since the strength of the reflected wave 36 is smaller than that of the ultrasonic wave 35 transmitted from the ultrasonic transducer device 4, the reception ultrasonic element 37 is shaped to easily respond to the reflected wave 36.

As the transmission ultrasonic element 34 and the reception ultrasonic element 37, a thin film piezoelectric element can be used. However, the transmission ultrasonic element 34 and the reception ultrasonic element 37 are not limited thereto. Alternatively, a transducer of a type using a capacitive element, such as a capacitive micro-machined ultrasonic transducer (c-MUT), may be adopted, or a bulk type piezoelectric element may be adopted.

The reflected wave 36 reaches a plurality of reception ultrasonic elements 37, and the plurality of reception ultrasonic elements 37 respond to the reflected wave 36. Then, each of the plurality of reception ultrasonic elements 37 outputs an ultrasonic signal corresponding to the reflected wave 36 to the multiplexing processing unit (multiplexer) 38.

The multiplexing processing unit 38 receives the electric signals output from the plurality of ultrasonic elements, time-division multiplexes the plurality of electric signals, and outputs a multiplexed signal obtained by the time-division multiplexing. Due to the multiplexing, it is possible to reduce the number of wirings 30. The number of signals to be multiplexed is not particularly limited. In the present embodiment, for example, the multiplexing processing unit 38 time-division multiplexes electric signals output from 64 reception ultrasonic elements 37 to obtain one electric signal. Then, the multiplexing processing unit 38 outputs the time-division multiplexed electric signal to the amplification unit 39.

The amplification unit 39 is not particularly limited as long as the amplification unit 39 is an amplifier circuit that amplifies electric power with little generation of noise. For example, a low noise amplifier (LNA) can be used as the amplification unit 39. The LNA amplifies a minute signal to a more useful level. The amplification unit 39 outputs the amplified electric signal to the second circuit board 7 of the input and output control unit 6 through the wiring 8.

A plurality of A/D conversion units 42, a plurality of demultiplexing processing units 43, and a first phasing addition circuit 44 as a plurality of combining processing circuits are provided on the second circuit board 7 of the input and output control unit 6, and these are connected to each other by the wiring 30 in this order. A serial conversion unit 45, a second electro-optical conversion unit 46, and a second light emitting unit 47 are provided so as to be connected to the first phasing addition circuit 44, and these are connected to each other by the wiring 30 in this order. The second electro-optical conversion unit 46 and the second light emitting unit 47 correspond to an electro-optical conversion unit.

The electric signal output from the reception ultrasonic element 37 is an analog signal. The A/D conversion unit 42 converts the analog signal into a digital signal and outputs the digital signal.

The first circuit board 5 and the second circuit board 7 are connected to each other by the wiring 8. The A/D conversion unit 42 is provided on the second circuit board 7. When the A/D conversion unit 42 performs conversion processing at high speed, the A/D conversion unit 42 generates heat. As a result, the temperature of the second circuit board 7 rises.

The reception ultrasonic element 37 is provided on the first circuit board 5. When the temperature of the reception ultrasonic element 37 rises, noise increases and accordingly the electric signal to be output fluctuates. As a result, the detection accuracy of the strength of the reflected wave 36 detected by the reception ultrasonic element 37 is lowered. On the other hand, the first circuit board 5 and the second circuit board 7 are separated from each other, but are connected to each other by the wiring 8. Therefore, even if the temperature of the second circuit board 7 rises, the temperature rise of the first circuit board 5 is suppressed. As a result, it is possible to suppress a lowering in the detection accuracy of the strength of the reflected wave 36 detected by the reception ultrasonic element 37.

The multiplexing processing unit 38 is provided on the first circuit board 5. Accordingly, since the amount of signals transmitted through the wiring 8 can be reduced, the wiring 8 can be made thin. As a result, it is possible to suppress the heat of the second circuit board 7 from conducting to the first circuit board 5.

The digital signal output from the A/D conversion unit 42 to the demultiplexing processing unit (demultiplexer) 43 is a parallel signal. The digital signal output from the A/D conversion unit 42 to the demultiplexing processing unit (demultiplexer) 43 is a parallel signal of the electric signal time-division multiplexed by the multiplexing processing unit 38. The demultiplexing processing unit 43 performs processing for returning the electric signal time-division multiplexed by the multiplexing processing unit 38 to the electric signal before the time-division multiplexing. In the present embodiment, for example, the demultiplexing processing unit 43 returns the time-division multiplexed electric signal to 64 electric signals. The signal input to the demultiplexing processing unit 43 is a digital parallel signal. The electric signal output from the demultiplexing processing unit 43 is also a digital parallel signal.

The first phasing addition circuit 44 receives the electric signal output from the demultiplexing processing unit 43. The electric signal is a digital parallel signal corresponding to the electric signals output from the plurality of reception ultrasonic elements 37. The first phasing addition circuit 44 receives the electric signals, shifts the plurality of electric signals in the time axis direction to combine the plurality of electric signals, and outputs a first composite signal as a composite signal. Due to the composite signal, it is possible to reduce the number of wirings through which the electric signals output from the plurality of reception ultrasonic elements 37 are transmitted. After the A/D conversion unit 42 outputs the digital signal, the combining processing circuit outputs the composite signal. The first phasing addition circuit 44 outputs the composite signal to the serial conversion unit 45.

Since the A/D conversion unit 42 outputs the digital parallel signal, the demultiplexing processing unit 43 and the first phasing addition circuit 44 perform processing on the digital parallel signal. The serial conversion unit 45 receives the digital parallel signal, and serializes the digital parallel signal to output a serial signal.

After the A/D conversion unit 42 outputs the digital signal, the first phasing addition circuit 44 outputs the composite signal. Since the first phasing addition circuit 44 can perform processing using a digital signal, the processing can be performed more easily compared with a case in which an analog signal is used. After the first phasing addition circuit 44 outputs the first composite signal as a composite signal, the serial conversion unit 45 serializes the digital signal to output a serial signal. Due to the serial signal, it is possible to reduce the number of signal wirings compared with a case of the parallel signal.

The second electro-optical conversion unit 46 and the second light emitting unit 47 have the same functions as those of the first electro-optical conversion unit 28 and the first light emitting unit 29 in the control unit 13, respectively. The second electro-optical conversion unit 46 receives the serial signal of the first composite signal and drives the second light emitting unit 47. The second electro-optical conversion unit 46 and the second light emitting unit 47 receive the composite signal, convert the composite signal into an optical signal, and output the optical signal. As described above, after the first phasing addition circuit 44 outputs the composite signal, the second electro-optical conversion unit 46 and the second light emitting unit 47 output the optical signal. The output optical signal is transmitted to the control unit 13 of the control device 3 through the optical cable 18.

The ultrasonic probe 2 includes two power supplies of a first power supply and a second power supply (not shown). The first power supply supplies electric power to the first circuit board 5, and the second power supply supplies electric power to the second circuit board 7. An analog circuit is provided on the first circuit board 5. Accordingly, an analog signal propagates through the first circuit board 5. A digital circuit is provided on the second circuit board 7. Accordingly, a digital signal propagates through the second circuit board 7. In the ultrasonic probe 2, power supplies for the first circuit board 5 and the second circuit board 7 are separated from each other. Therefore, it is possible to prevent the noise of the digital circuit of the second circuit board 7 from propagating to the analog circuit of the first circuit board 5 through the power supply.

A second light receiving unit 48, a second photoelectric conversion unit 49, a parallel conversion unit 50, a second phasing addition circuit 51, and an image processing unit 52 are provided in the control unit 13, and these are connected to each other by the wiring 30 in this order. The second light receiving unit 48 and the second photoelectric conversion unit 49 form a photoelectric conversion unit. The image processing unit 52 is connected to the display unit 17. The second light receiving unit 48 and the second light emitting unit 47 are connected to each other by the optical cable 18.

The second light receiving unit 48 and the second photoelectric conversion unit 49 have the same functions as those of the first light receiving unit 31 and the first photoelectric conversion unit 32 provided on the second circuit board 7, respectively. The second light receiving unit 48 and the second photoelectric conversion unit 49 receive an optical signal, and convert the optical signal into an electric signal. The electric signal is a digital serial signal.

The parallel conversion unit 50 converts the digital serial signal into a digital parallel signal. Since the parallel conversion unit 50 converts the serial signal into the parallel signal, the second phasing addition circuit 51 and the image processing unit 52 can easily perform arithmetic processing.

The second phasing addition circuit 51 receives the first composite signals that are electric signals, shifts the plurality of electric signals in the time axis direction to combine the plurality of electric signals, and outputs a second composite signal. The first phasing addition circuit 44 combines electric signals corresponding to the reflected waves 36 received by the reception ultrasonic elements 37 aligned in the row direction, and outputs a first composite signal. Therefore, the first composite signal is output to each reception ultrasonic element 37 in each row. Then, the second phasing addition circuit 51 combines the first composite signals corresponding to the reception ultrasonic elements 37 in each column, and outputs a second composite signal to the image processing unit 52.

That is, the plurality of reception ultrasonic elements 37 arranged in a matrix receive the reflected wave 36 that is reflected at a certain place on the interface 25a. Then, the first phasing addition circuit 44 and the second phasing addition circuit 51 combine the electric signals output from the respective reception ultrasonic elements 37 to form one second composite signal. The second composite signal is a signal in which ultrasonic signals of the reflected waves 36 received by the group of the reception ultrasonic elements 37 are collected.

The transmission control unit 26 controls a place where the ultrasonic waves 35 emitted from the transmission ultrasonic elements 34 converge. The transmission control unit 26 scans the place where the ultrasonic waves 35 converge in the row and column directions in which the transmission ultrasonic elements 34 are aligned. The place where the ultrasonic waves 35 converge is scanned in the depth direction by gradually changing the distance from the ultrasonic transducer device 4. As a result, the transmission control unit 26 scans the place where the ultrasonic waves 35 converge in a three-dimensional manner.

The image processing unit 52 receives an electric signal, which indicates the strength of the reflected wave 36 that is reflected at each place of the space on the +Z-direction side of the ultrasonic transducer device 4, from the second phasing addition circuit 51. The image processing unit 52 calculates a cross-sectional view obtained by cutting the strength distribution of the three-dimensional reflected wave 36 with a predetermined plane. The image processing unit 52 calculates a perspective view of the strength distribution of the three-dimensional reflected wave 36. Then, the cross-sectional view and the perspective view are output to the display unit 17. The display unit 17 displays the cross-sectional view and the perspective view of the three-dimensional image showing the strength distribution of the reflected wave 36. The operator observes the cross-sectional view and the perspective view to check the state of the interface 25a of the subject 25.

Figure 3:
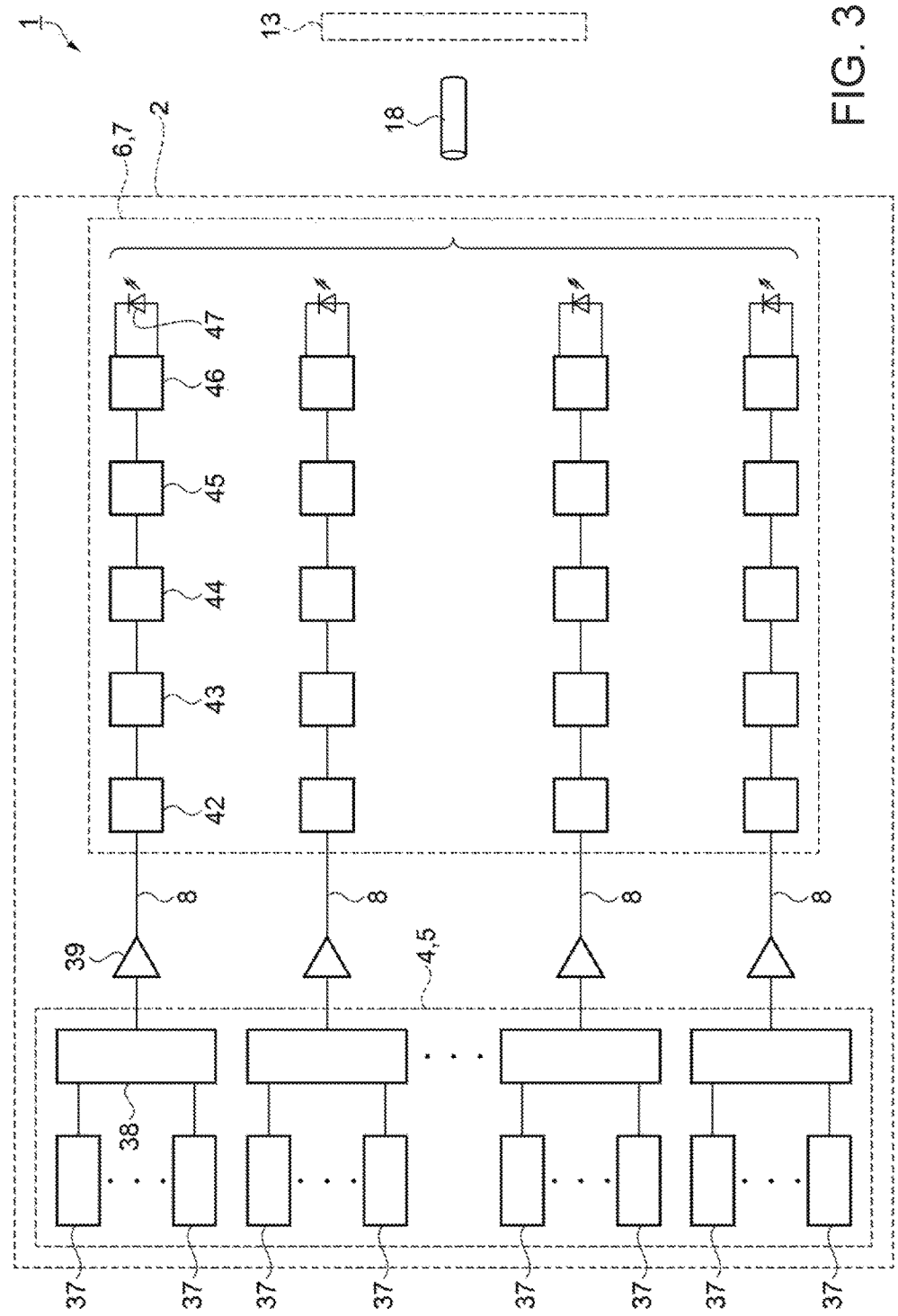
FIG. 3 is a block diagram showing circuits on a first circuit board and a second circuit board.

FIG. 3 is a block diagram showing circuits on the first circuit board and the second circuit board. As shown in FIG. 3, a plurality of reception ultrasonic elements 37, a plurality of multiplexing processing units 38, and a plurality of amplification units 39 are provided on the first circuit board 5. The number of reception ultrasonic elements 37, the number of multiplexing processing units 38, and the number of amplification units 39 are not particularly limited. In the present embodiment, for example, the reception ultrasonic elements 37 are arranged in a matrix in 64 rows by columns on the first circuit board 5. 64 reception ultrasonic elements 37 are connected to one multiplexing processing unit 38. The 64 reception ultrasonic elements 37 form one matrix-like row.

64 multiplexing processing units 38 are provided on the first circuit board 5, and the reception ultrasonic elements 37 in each row are connected to the different multiplexing processing units 38. 64 amplification units 39 are provided in the multiplexing processing unit 38. One multiplexing processing unit 38 is connected to one amplification unit 39. Since one wiring 8 is connected to one amplification unit 39, the first circuit board 5 and the second circuit board 7 are connected to each other by 64 wiring 8.

The A/D conversion unit 42, the demultiplexing processing unit 43, the first phasing addition circuit 44, the serial conversion unit 45, and the second electro-optical conversion unit 46 are connected in series to each wiring 8 connected to the amplification unit 39. The second light emitting unit 47 is provided in each second electro-optical conversion unit 46.

Since the reception ultrasonic elements 37 are arranged in 64 rows by 64 columns, the number of reception ultrasonic elements 37 is 4096. On the other hand, the number of wirings 8 is 64, which is smaller than the number of reception ultrasonic elements 37. By reducing the number of wirings 8, heat transfer from the second circuit board 7 to the first circuit board 5 through the wiring 8 is suppressed. Therefore, even if the A/D conversion unit 42 generates heat, it is possible to suppress generating noise of the reception ultrasonic element 37 due to heat.

Since the number of second light emitting units 47 is 64, the number of optical cables 18 is also 64. The smaller the number of optical cables 18 is, the easier the optical cable 18 is deformed. Accordingly, the ultrasonic probe 2 can be easily operated.

Figure 4:
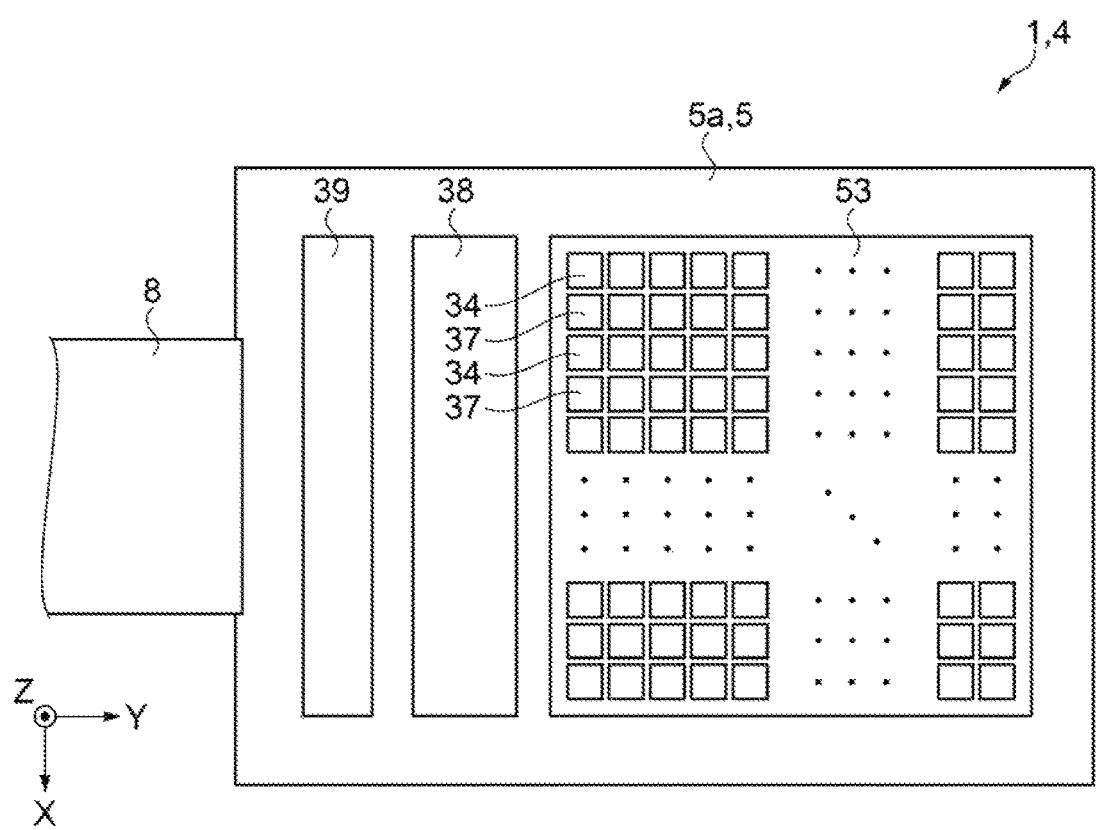
FIG. 4 is a schematic plan view showing the structure of the first circuit board.

FIG. 4 is a schematic plan view showing the structure of the first circuit board. A reception ultrasonic element substrate 53, the multiplexing processing unit 38, and the amplification unit 39 are provided on a first surface 5a of the first circuit board 5. A plurality of transmission ultrasonic elements 34 and a plurality of reception ultrasonic elements 37 are alternately provided on the reception ultrasonic element substrate 53.

Figure 5:
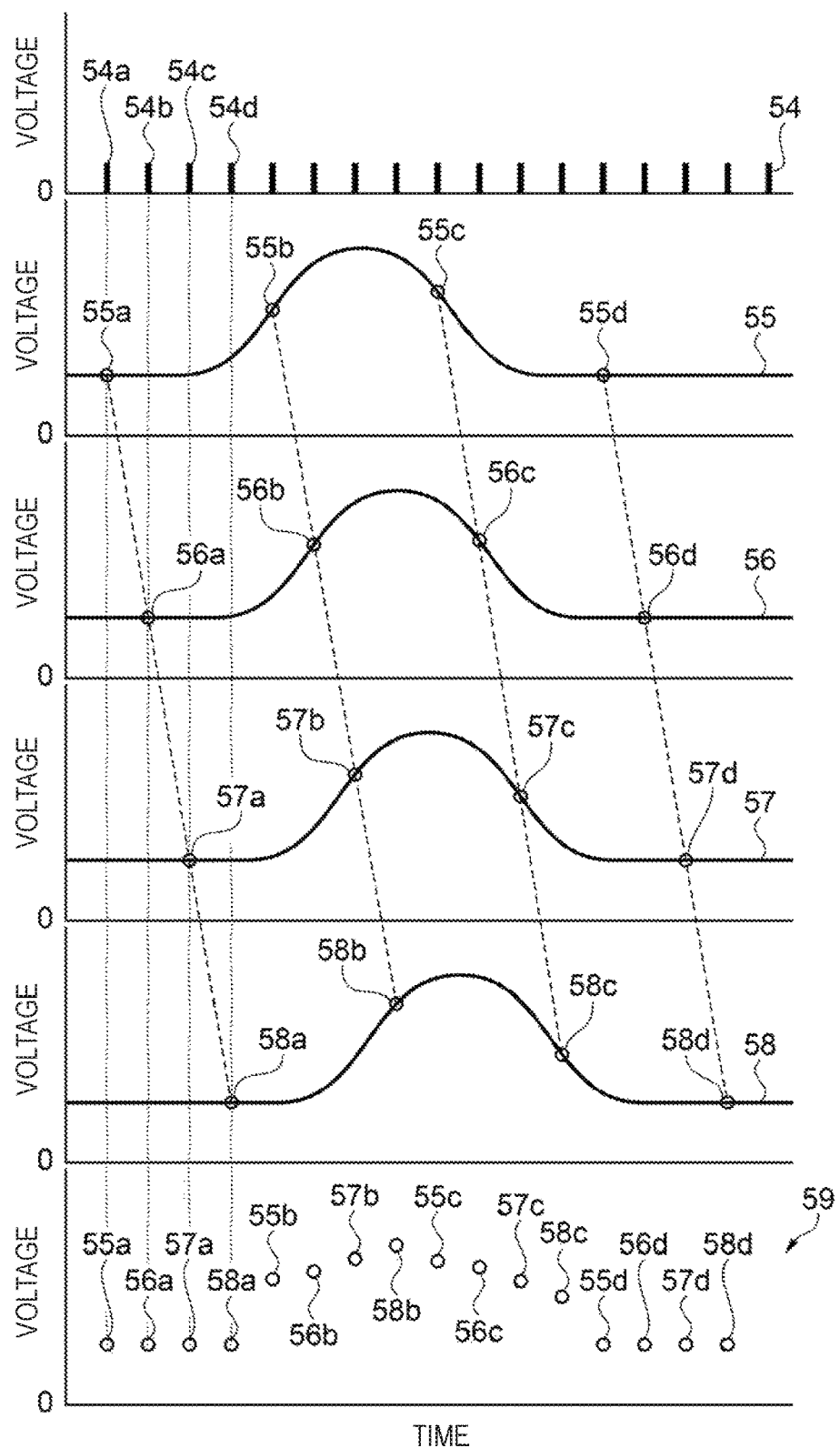
FIG. 5 is a diagram for explaining the function of a multiplexing processing unit.

FIG. 5 is a diagram for explaining the function of the multiplexing processing unit. Six time charts are shown in FIG. 5. The horizontal axis of each time chart indicates the passage of time, and the time transitions to the right side from the left side in the diagram. The vertical axis indicates a voltage. An upper sampling line 54 is a line indicating the timing at which the multiplexing processing unit 38 samples the output voltage of the reception ultrasonic element 37. The multiplexing processing unit 38 samples the output voltage of the reception ultrasonic element 37 at the timing at which the sampling line 54 rises. The sampling line 54 shows a waveform in which rectangular waves are provided at equal intervals.

First to fourth reflected wave signals 55 to 58 located below the sampling line 54 in FIG. 5 are electric signals output to the multiplexing processing unit 38 by the reception ultrasonic element 37. Since the electric signal is output from each reception ultrasonic element 37, the electric signal is output to the multiplexing processing unit 38. In the present embodiment, one multiplexing processing unit 38 multiplexes 64 electric signals to obtain one electric signal. However, in order to make the explanation easy to understand, the following explanation will be given using an example of multiplexing four electric signals to obtain one electric signal. In FIG. 5, a plot 59 located below the fourth reflected wave signal 58 shows a data string obtained by the combination of the multiplexing processing unit 38.

At a first point in time 54a of the sampling line 54, the multiplexing processing unit 38 applies a voltage of the first reflected wave signal 55 to the plot 59 as an eleventh voltage 55a. Then, at a second point in time 54b of the sampling line 54, the multiplexing processing unit 38 applies a voltage of the second reflected wave signal 56 to the plot 59 as a twenty-first voltage 56a. Then, at a third point in time 54c of the sampling line 54, the multiplexing processing unit 38 applies a voltage of the third reflected wave signal 57 to the plot 59 as a thirty-first voltage 57a. Then, at a fourth point in time 54d of the sampling line 54, the multiplexing processing unit 38 applies a voltage of the fourth reflected wave signal 58 to the plot 59 as a forty-first voltage 58a.

In this manner, voltages are sequentially applied to the plot 59 from the first to fourth reflected wave signals 55 to 58 in accordance with the timing indicated by the sampling line 54. Then, after sampling from the fourth reflected wave signal 58, voltages of the first to fourth reflected wave signals 55 to 58 are further sampled and are sequentially applied to the plot 59. As a result, a twelfth voltage 55$b$, a twenty-second voltage 56$b$, a thirty-second voltage 57$b$, and a forty-second voltage 58$b$ are applied to the plot 59.

A thirteenth voltage 55$c$, a twenty-third voltage 56$c$, a thirty-third voltage 57$c$, and a forty-third voltage 58$c$ are applied to the plot 59 in the same procedure. Then, a fourteenth voltage 55$d$, a twenty-fourth voltage 56$d$, a thirty-fourth voltage 57$d$, and a forty-fourth voltage 58$d$ are applied to the plot 59. The multiplexing processing unit 38 samples a voltage and applies the voltage to the plot 59 until the electric signals of the first to fourth reflected wave signals 55 to 58 end. As a result, data in which the electric signals of the first to fourth reflected wave signals 55 to 58 are sequentially arranged at predetermined intervals appears in the plot 59. The data indicated by the plot 59 is data including the first to fourth reflected wave signals 55 to 58, and is compressed data.

The electric signal indicated by the plot 59 is input to the demultiplexing processing unit 43 through the amplification unit 39 and the A/D conversion unit 42. The demultiplexing processing unit 43 performs processing reverse to the processing performed by the multiplexing processing unit 38. The demultiplexing processing unit 43 restores the first reflected wave signal 55 by connecting the pieces of data of the eleventh voltage 55$a$, the twelfth voltage 55$b$, the thirteenth voltage 55$c$, and the fourteenth voltage 55$d$ in the plot 59. The demultiplexing processing unit 43 restores the second reflected wave signal 56 by connecting the pieces of data of the twenty-first voltage 56$a$, the twenty-second voltage 56$b$, the twenty-third voltage 56$c$, and the twenty-fourth voltage 56$d$ in the plot 59.

The demultiplexing processing unit 43 restores the third reflected wave signal 57 by connecting the pieces of data of the thirty-first voltage 57$a$, the thirty-second voltage 57$b$, the thirty-third voltage 57$c$, and the thirty-fourth voltage 57$d$ in the plot 59. The demultiplexing processing unit 43 restores the fourth reflected wave signal 58 by connecting the pieces of data of the forty-first voltage 58$a$, the forty-second voltage 58$b$, the forty-third voltage 58$c$, and the forty-fourth voltage 58$d$ in the plot 59. In this manner, the demultiplexing processing unit 43 restores the first to fourth reflected wave signals 55 to 58.

Figure 6:
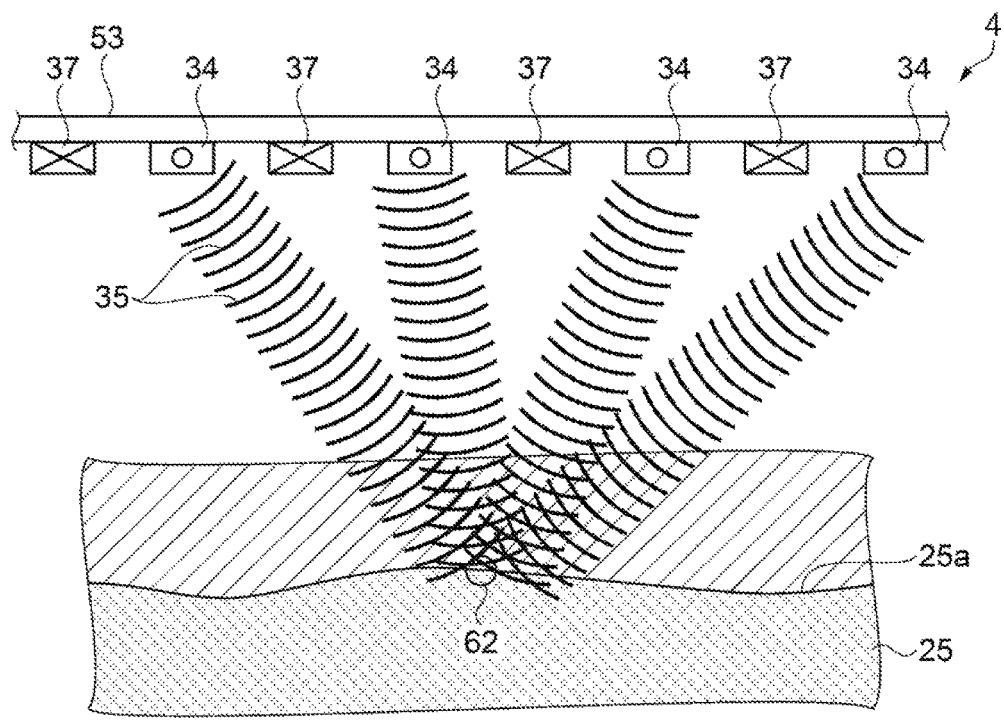
FIG. 6 is a schematic diagram for explaining the emission of ultrasonic waves in an ultrasonic transducer device.

FIG. 6 is a schematic diagram for explaining the emission of ultrasonic waves in the ultrasonic transducer device. As shown in FIG. 6, the transmission ultrasonic element 34 and the reception ultrasonic element 37 are alternately arranged on the reception ultrasonic element substrate 53. A plurality of transmission ultrasonic elements 34 emit the ultrasonic wave 35 while shifting the timing. An instruction regarding the timing of the ultrasonic wave 35 emitted from the transmission ultrasonic element 34 is given by the transmission control unit 26. The timing is controlled such that the transmission ultrasonic element 34 emits the ultrasonic wave 35 in two directions of X and Y directions.

The strength of the wave increases at a place where places that become the belly of the wave overlap when a plurality of ultrasonic waves 35 overlap each other. The transmission control unit 26 controls the timing at which each transmission ultrasonic element 34 emits the ultrasonic wave 35 so that the strength of the ultrasonic wave 35 increases at a specific place. By controlling the timing in this manner, the strength of the ultrasonic wave 35 emitted from the ultrasonic transducer device 4 is maximized at a convergence point 62. The transmission control unit 26 moves the position of the convergence point 62 in the X and Y directions to perform a scan. The transmission control unit 26 also moves the position of the convergence point 62 in the Z direction to perform a scan.

Figure 7:
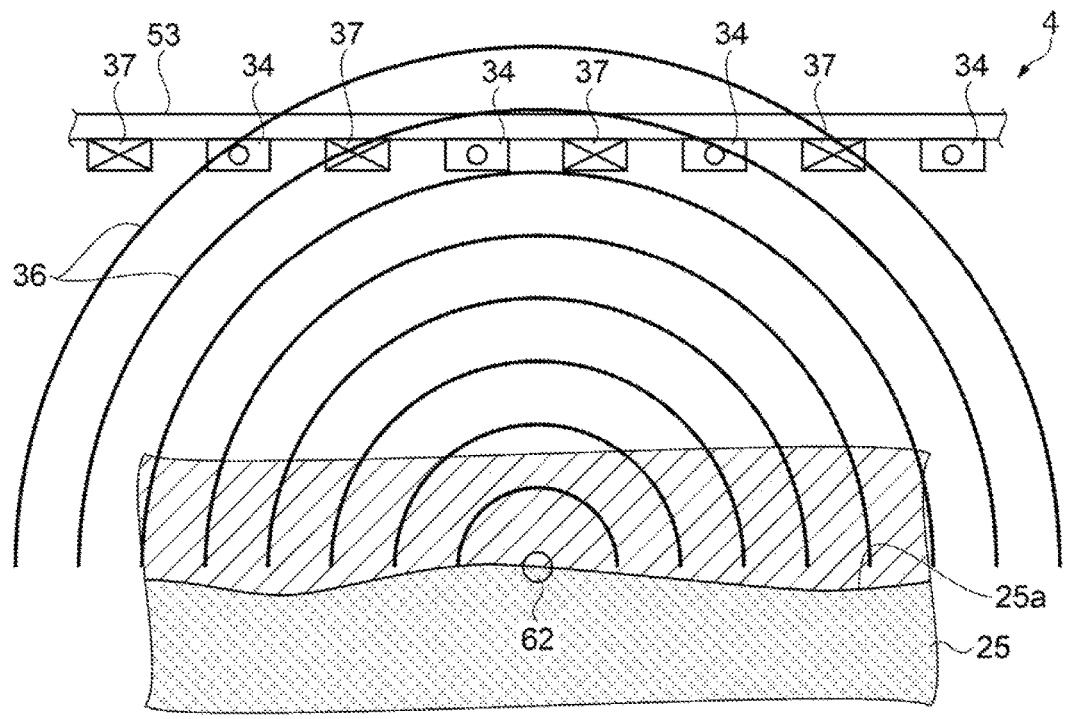
FIG. 7 is a schematic diagram for explaining the reception of ultrasonic waves in the ultrasonic transducer device.

FIG. 7 is a schematic diagram for explaining the reception of ultrasonic waves in the ultrasonic transducer device. As shown in FIG. 7, when the convergence point 62 is located on the interface 25$a$, the strong reflected wave 36 travels from the convergence point 62 toward the ultrasonic transducer device 4. The distance between the plurality of reception ultrasonic elements 37 on the reception ultrasonic element substrate 53 and the convergence point 62 differs depending on each reception ultrasonic element 37. Therefore, the time at which each reception ultrasonic element 37 receives the reflected wave 36 is shifted. The amount of time shift is an amount obtained by dividing the distance between the convergence point 62 and each reception ultrasonic element 37 by the speed of the reflected wave 36.

Since the position of the convergence point 62 is controlled by the transmission control unit 26, the position of the convergence point 62 is known. Accordingly, the relative position between the convergence point 62 and each reception ultrasonic element 37 is also known. Therefore, the difference in time at which the reflected wave 36 reaches each reception ultrasonic element 37 is also known.

Figure 8:
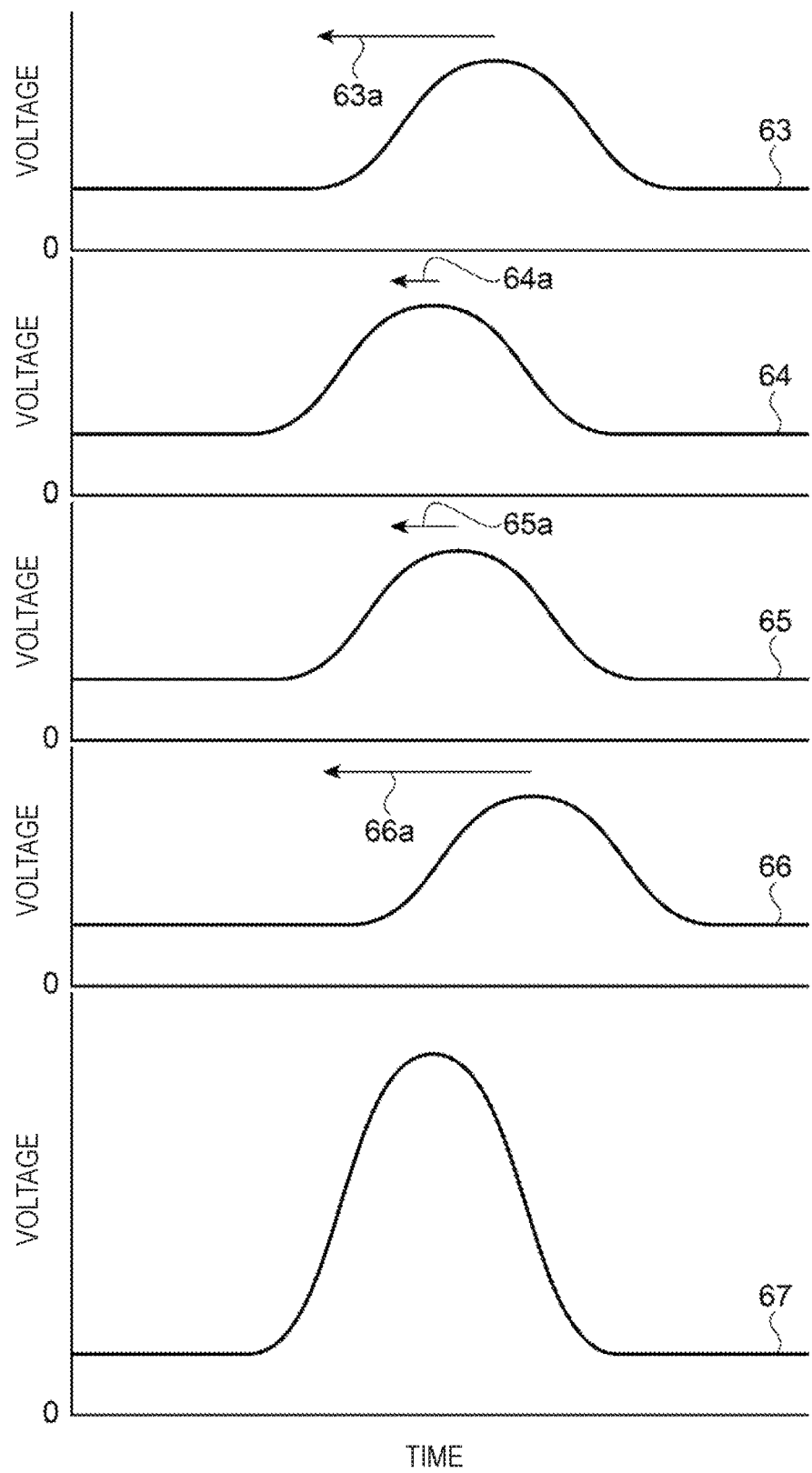
FIG. 8 is a diagram for explaining the function of a first phasing addition circuit.

FIG. 8 is a diagram for explaining the function of the first phasing addition circuit. Five time charts are shown in FIG. 8. The horizontal axis of each time chart indicates the passage of time, and the time transitions to the right side from the left side in the diagram. The vertical axis indicates a voltage. A first reflected wave line 63, a second reflected wave line 64, a third reflected wave line 65, and a fourth reflected wave line 66 on the upper side indicate four of the reflected waves 36 received by the reception ultrasonic elements 37. The reception ultrasonic elements 37 are arranged from the first row to the sixty-fourth row. These four waveforms are digital signals of electric signals output from the reception ultrasonic elements 37 aligned in the same first row. These four waveforms indicate some of the waveforms of the electric signals input to the first phasing addition circuit 44. In the present embodiment, one first phasing addition circuit 44 adds 64 electric signals to obtain one first composite signal. However, in order to make the explanation easy to understand, the following explanation will be given using an example of adding four electric signals to obtain one first composite signal.

The second reflected wave line 64 and the third reflected wave line 65 are waveforms of the reception ultrasonic elements 37 located near the convergence point 62. The first reflected wave line 63 and the fourth reflected wave line 66 are waveforms of the reception ultrasonic elements 37 away from the convergence point 62. The first phasing addition circuit 44 receives data of the relative position between each reception ultrasonic element 37 and the convergence point 62 from the transmission control unit 26. Then, the first phasing addition circuit 44 calculates the correction amount of each waveform of the fourth reflected wave line 63 from the first reflected wave line 66. The correction amount to be calculated is a correction amount for the reflected wave 36 that the reception ultrasonic element 37 receives when the reception ultrasonic element 37 is located at a place facing the convergence point 62.

A first correction amount 63$a$ is the correction amount of the first reflected wave line 63, and a second correction amount 64$a$ is the correction amount of the second reflected wave line 64. A third correction amount 65$a$ is the correction amount of the third reflected wave line 65, and a fourth correction amount 66$a$ is the correction amount of the fourth reflected wave line 66. Since the second reflected wave line 64 and the third reflected wave line 65 are waveforms received by the reception ultrasonic elements 37 located near the convergence point 62, the second correction amount 64*a* and the third correction amount 65*a* are a short time. Since the first reflected wave line 63 and the fourth reflected wave line 66 are waveforms received by the reception ultrasonic elements 37 away from the convergence point 62, the first correction amount 63*a* and the fourth correction amount 66*a* are a long time.

The first phasing addition circuit 44 receives the electric signals output from the plurality of reception ultrasonic elements 37. Then, the plurality of electric signals are shifted in the time axis direction and are combined, and a composite signal is output. Specifically, the first phasing addition circuit 44 shifts the first reflected wave line 63 in the time axis direction by the time of the first correction amount 63*a*. The first phasing addition circuit 44 shifts the second reflected wave line 64 in the time axis direction by the time of the second correction amount 64*a*. The first phasing addition circuit 44 shifts the third reflected wave line 65 in the time axis direction by the time of the third correction amount 65*a*. The first phasing addition circuit 44 shifts the fourth reflected wave line 66 in the time axis direction by the time of the fourth correction amount 66*a*. Then, voltages at the respective times of the first reflected wave line 63 to the fourth reflected wave line 66 that have been shifted in the time axis direction are added. As described above, other waveforms are also shifted in the time axis direction. Then, voltages at the respective times of the reflected wave lines that have been shifted in the time axis direction are added.

In the above calculation, a procedure for combining the four voltage signals in the first row is shown. Since 64 reception ultrasonic elements 37 are arranged in the first row of the reception ultrasonic elements 37, 64 reflection lines are time-corrected and added. As a result, a row composite reflected wave line 67 is obtained. The row composite reflected wave line 67 is a result of the combination of the outputs of the reception ultrasonic elements 37 in the first row. The row composite reflected wave line 67 in the reception ultrasonic element 37 in the first row is assumed to be a first row reflection line. Since the ultrasonic transducer device 4 has 64 rows of reception ultrasonic elements 37, the row composite reflected wave line 67 is also calculated using the same method in the second to sixty-fourth rows. Then, a second row reflection line to a sixty-fourth row reflection line corresponding to the row composite reflected wave lines 67 of the second to sixty-fourth rows are calculated. The first row reflection line to the sixty-fourth row reflection line indicate the first composite signal as a composite signal.

Figure 9:
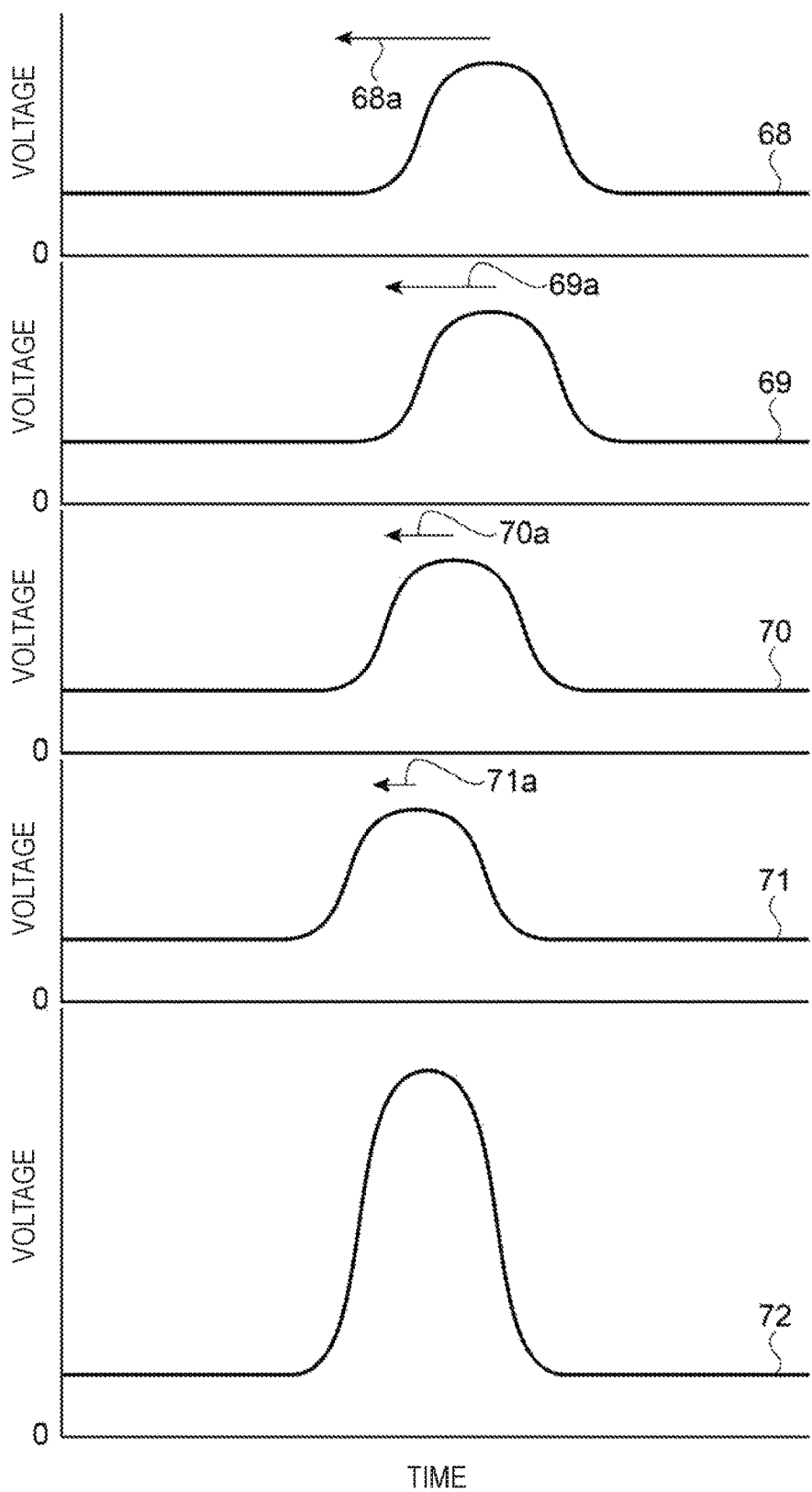
FIG. 9 is a diagram for explaining the function of a second phasing addition circuit.

FIG. 9 is a diagram for explaining the function of the second phasing addition circuit. Five time charts are shown in FIG. 9. The horizontal axis of each time chart indicates the passage of time, and the time transitions to the right side from the left side in the diagram. The vertical axis indicates a voltage. A first row reflected wave line 68, a second row reflected wave line 69, a third row reflected wave line 70, and a fourth row reflected wave line 71 on the upper side show four examples in the row composite reflected wave line 67 obtained by the calculation and combination of the first phasing addition circuit 44. In the present embodiment, one second phasing addition circuit 51 adds 64 row composite reflected wave lines 67 to obtain one second composite signal. However, in order to make the explanation easy to understand, the following explanation will be given using an example of adding four row composite reflected wave lines 67 to obtain one second composite signal.

The fourth row reflected wave line 71 is a waveform of the row composite reflected wave line 67 in a row near the convergence point 62. The third row reflected wave line 70, the second row reflected wave line 69, and the first row reflected wave line 68 are waveforms of the row composite reflected wave line 67 in rows away from the convergence point 62 in this order. The first phasing addition circuit 44 receives data of the relative position between each row of the reception ultrasonic element 37 and the convergence point 62 from the transmission control unit 26. Then, the second phasing addition circuit 51 calculates the correction amount of each waveform of the first row reflected wave line 68 to the fourth row reflected wave line 71. The correction amount to be calculated is a correction amount for the reflected wave 36 that the reception ultrasonic element 37 receives when the reception ultrasonic element 37 is located at a place facing the convergence point 62.

A first row correction amount 68*a* is the correction amount of the first row reflected wave line 68, and a second row correction amount 69*a* is the correction amount of the second row reflected wave line 69. A third row correction amount 70*a* is the correction amount of the third row reflected wave line 70, and a fourth row correction amount 71*a* is the correction amount of the fourth row reflected wave line 71. Since the correction amount becomes smaller as the row becomes closer to the convergence point 62, the first row correction amount 68*a* is a long time and the fourth row correction amount 71*a* is a short time.

The second phasing addition circuit 51 receives the first composite signal output from the first phasing addition circuit 44. Then, the plurality of first composite signals are shifted in the time axis direction and are combined, and a composite signal is output. Specifically, the second phasing addition circuit 51 shifts the first row reflected wave line 68 in the time axis direction by the time of the first row correction amount 68*a*. The second phasing addition circuit 51 shifts the second row reflected wave line 69 in the time axis direction by the time of the second row correction amount 69*a*. The second phasing addition circuit 51 shifts the third row reflected wave line 70 in the time axis direction by the time of the third row correction amount 70*a*. The second phasing addition circuit 51 shifts the fourth row reflected wave line 71 in the time axis direction by the time of the fourth row correction amount 71*a*. Then, voltages at the respective times of the first row reflected wave line 68 to the fourth row reflected wave line 71 that have been shifted in the time axis direction are added. As described above, other waveforms are also shifted in the time axis direction. Then, voltages at the respective times of the reflected wave lines that have been shifted in the time axis direction are added.

In the above calculation, a procedure for combining the four first composite signals in the first to fourth rows is shown. Since 64 rows of reception ultrasonic elements 37 are arranged in the ultrasonic transducer device 4, 64 rows of first composite signals are time-corrected and added. As a result, a composite reflected wave line 72 is obtained. The composite reflected wave line 72 is a result of the combination of the outputs of all of the reception ultrasonic elements 37 provided in the ultrasonic transducer device 4. By the above procedure, the composite reflected wave line 72 corresponding to one convergence point 62 is obtained. The voltage of the peak value of the composite reflected wave line 72 is set as the strength of the reflected wave 36 at the convergence point 62.

The transmission control unit 26 scans the convergence point 62 in the X and Y directions. The transmission control unit 26 scans the convergence point 62 in the X and Y directions while changing the depth of the convergence point 62. Then, the strength of the reflected wave 36 at each convergence point 62 is calculated. When the strength of the reflected wave 36 in a region set in advance can be measured, the image processing unit 52 calculates a strength distribution image of the reflected wave 36 and displays the strength distribution image on the display unit 17.

As described above, according to the present embodiment, the following effect is obtained.

(1) According to the present embodiment, the ultrasonic measurement apparatus 1 includes the first phasing addition circuit 44, the second electro-optical conversion unit 46, the second light emitting unit 47, the optical cable 18, the second light receiving unit 48, and the second photoelectric conversion unit 49. The first phasing addition circuit 44 receives the electric signals output from the plurality of reception ultrasonic elements 37. Then, the first phasing addition circuit 44 shifts the electric signals in the time axis direction to combine the electric signals. Then, the first composite signal is output. The second electro-optical conversion unit 46 and the second light emitting unit 47 receive the first composite signal. Then, the first composite signal is converted into an optical signal. The optical signal is transmitted through the optical cable 18. The second light receiving unit 48 and the second photoelectric conversion unit 49 receive the optical signal, and convert the optical signal into an electric signal.

The ultrasonic wave 35 emitted from the transmission ultrasonic element 34 is reflected by the interface 25a, and the reflected wave 36 is received by the reception ultrasonic element 37. In this case, the reception ultrasonic element 37, which is far from the reflection place of the reflected wave 36, receives the reflected wave 36 later than the reception ultrasonic element 37 close to the reflection place of the reflected wave 36. Therefore, the first composite signal obtained by combining the electric signals, which are received and output by the respective reception ultrasonic elements 37, by shifting the electric signals in the time axis direction is a signal that includes distance information between the reception ultrasonic element 37 and the reflection place of the ultrasonic wave 35 and that has a high signal strength compared with noise.

Since each of the reception ultrasonic elements 37 outputs an electric signal, the number of electric signals output from the group of the reception ultrasonic elements 37 increases as the number of reception ultrasonic elements 37 increases. Then, the first phasing addition circuit 44 combines the plurality of electric signals to obtain the first composite signal. In this manner, it is possible to reduce the amount of electric signals transmitted through the optical cable 18. Then, the second electro-optical conversion unit 46 and the second light emitting unit 47 convert the first composite signal into an optical signal, and transmit the optical signal through the optical cable 18. The second light receiving unit 48 and the second photoelectric conversion unit 49 receive the optical signal, and convert the optical signal into an electric signal. The electric signal is the first composite signal. In this manner, it is possible to utilize the first composite signal obtained by combining the electric signals output from the respective reception ultrasonic elements 37.

When the electric signal output from the reception ultrasonic element 37 is transmitted as it is, the number of wirings for transmission is increased. For the wiring of the electric signal, metal is used. Therefore, if the number of wirings is large, it is difficult for the wirings to bend. For this reason, the operability is lowered. In the ultrasonic measurement apparatus 1, instead of the electric signal, the optical signal is transmitted through the optical cable 18. Since a thin wire, such as a glass wire or a transparent resin wire, can be used for the optical cable 18, the optical cable 18 can be made thin so as to be able to bend. Since the first phasing addition circuit 44 combines the electric signals before the second electro-optical conversion unit 46 and the second light emitting unit 47 output the optical signal, it is possible to reduce the amount of optical signals to be transmitted. As a result, since the optical cable 18 can be made thin so as to be able to bend, the ultrasonic measurement apparatus 1 having good operability can be obtained.

(2) According to the present embodiment, the electric signal output from the reception ultrasonic element 37 is an analog signal. The ultrasonic measurement apparatus 1 includes the A/D conversion unit 42 and the serial conversion unit 45. The A/D conversion unit 42 converts the analog signal into a digital signal. By using a digital arithmetic device, an advanced calculation is performed on the digital signal. As a result, it is possible to form an ultrasonic cross-sectional image. After the A/D conversion unit 42 outputs the digital signal, the first phasing addition circuit 44 outputs the first composite signal. Since the first phasing addition circuit 44 can perform processing using a digital signal, the processing can be performed more easily compared with a case in which an analog signal is used. After the first phasing addition circuit 44 outputs the first composite signal, the serial conversion unit 45 serializes the digital signal to output a serial signal. Due to the serial signal, it is possible to reduce the number of signal wirings compared with a case of the parallel signal. As a result, since the optical cable 18 can be made thin so as to be able to bend, the ultrasonic measurement apparatus 1 having good operability can be obtained.

(3) According to the present embodiment, the ultrasonic measurement apparatus 1 includes the first circuit board 5 and the second circuit board 7. The reception ultrasonic element 37 is provided on the first circuit board 5. The A/D conversion unit 42 is provided on the second circuit board 7. The first circuit board 5 and the second circuit board 7 are separated from each other, but are connected to each other by the wiring 8. When the A/D conversion unit 42 performs conversion processing at high speed, the A/D conversion unit 42 generates heat. As a result, the temperature of the second circuit board 7 rises.

The reception ultrasonic element 37 is provided on the first circuit board 5. When the temperature of the reception ultrasonic element 37 rises, noise increases and accordingly the electric signal to be output fluctuates. As a result, the detection accuracy of the strength of the reflected wave 36 detected by the reception ultrasonic element 37 is lowered. On the other hand, the first circuit board 5 and the second circuit board 7 are separated from each other, but are connected to each other by the wiring 8. Therefore, even if the temperature of the second circuit board 7 rises, the temperature rise of the first circuit board 5 is suppressed. As a result, it is possible to suppress a lowering in the detection accuracy of the strength of the reflected wave 36 detected by the reception ultrasonic element 37.

(4) According to the present embodiment, the second circuit board 7 includes the second heat dissipation unit 10, and the second heat dissipation unit 10 dissipates the heat of the second circuit board 7. Therefore, it is possible to suppress the temperature rise of the second circuit board 7.

(5) According to the present embodiment, the first circuit board 5 includes the first heat dissipation unit 9, and the first heat dissipation unit 9 dissipates the heat of the first circuit board 5. Therefore, it is possible to suppress the temperature rise of the first circuit board 5.

(6) According to the present embodiment, the heat insulation unit 24 is provided between the first circuit board 5 and the second circuit board 7, and the heat insulation unit 24 blocks conductive heat transferred from the second circuit board 7 to the first circuit board 5. Therefore, even if the temperature of the second circuit board 7 rises, it is possible to suppress the temperature rise of the first circuit board 5.

(7) According to the present embodiment, the ultrasonic measurement apparatus 1 includes the first circuit board 5 and the second circuit board 7. The reception ultrasonic element 37 is provided on the first circuit board 5. The A/D conversion unit 42 is provided on the second circuit board 7. The first circuit board 5 and the second circuit board 7 are separated from each other, but are connected to each other by the wiring 8. When the A/D conversion unit 42 performs conversion processing at high speed, the A/D conversion unit 42 generates heat. As a result, the temperature of the second circuit board 7 rises.

The first circuit board 5 and the second circuit board 7 are separated from each other, but are connected to each other by the wiring 8. Therefore, even if the temperature of the second circuit board 7 rises, the temperature rise of the first circuit board 5 is suppressed. As a result, it is possible to suppress a lowering in the detection accuracy of the strength of the reflected wave 36 detected by the reception ultrasonic element 37.

The multiplexing processing unit 38 is provided on the first circuit board 5. Accordingly, since the amount of signals transmitted through the wiring 8 can be reduced, the wiring 8 can be made thin. As a result, it is possible to suppress conducting the heat of the second circuit board 7 to the first circuit board 5.

(8) According to the present embodiment, the ultrasonic probe 2 includes the first phasing addition circuit 44, the second electro-optical conversion unit 46, and the second light emitting unit 47. The first phasing addition circuit 44 receives the electric signals output from the plurality of reception ultrasonic elements 37. Then, the first phasing addition circuit 44 shifts the electric signals in the time axis direction to combine the electric signals. Then, the first composite signal is output. The second electro-optical conversion unit 46 and the second light emitting unit 47 receive the first composite signal. Then, the first composite signal is converted into an optical signal. The optical signal is transmitted through the optical cable 18.

The ultrasonic wave 35 emitted from the transmission ultrasonic element 34 is reflected by the interface 25a, and the reflected wave 36 is received by the reception ultrasonic element 37. In this case, the reception ultrasonic element 37, which is far from the reflection place of the reflected wave 36, receives the reflected wave 36 later than the reception ultrasonic element 37 close to the reflection place of the reflected wave 36. Therefore, the first composite signal obtained by combining the electric signals, which are received and output by the respective reception ultrasonic elements 37, by shifting the electric signals in the time axis direction is a signal that includes distance information between the reception ultrasonic element 37 and the reflection place of the ultrasonic wave 35 and that has a high signal strength compared with noise.

Since each of the reception ultrasonic elements 37 outputs an electric signal, the number of electric signals output from the group of the reception ultrasonic elements 37 increases as the number of reception ultrasonic elements 37 increases. Then, the first phasing addition circuit 44 combines the plurality of electric signals to obtain the first composite signal. In this manner, it is possible to reduce the amount of electric signals transmitted through the optical cable 18. Then, the second electro-optical conversion unit 46 and the second light emitting unit 47 convert the first composite signal into an optical signal, and transmit the optical signal through the optical cable 18.

When the electric signal output from the reception ultrasonic element 37 is transmitted as it is, the number of wirings for transmission is increased. For the wiring of the electric signal, metal is used. Therefore, if the number of wirings is large, it is difficult for the wirings to bend. For this reason, the operability is lowered. In the ultrasonic measurement apparatus 1, instead of the electric signal, the optical signal is transmitted through the optical cable 18. Since a thin wire, such as a glass wire or a transparent resin wire, can be used for the optical cable 18, the optical cable 18 can be made thin so as to be able to bend. Since the first phasing addition circuit 44 combines the electric signals before the second electro-optical conversion unit 46 and the second light emitting unit 47 output the optical signal, it is possible to reduce the amount of optical signals to be transmitted. As a result, since the optical cable 18 can be made thin so as to be able to bend, the ultrasonic probe 2 having good operability can be obtained.

Second Embodiment

Next, an embodiment of the ultrasonic measurement apparatus will be described with reference to an electric block diagram of an ultrasonic measurement apparatus shown in FIG. 10. The present embodiment is different from the first embodiment in that the demultiplexing processing unit 43 shown in FIG. 2 is provided in the control unit 13 instead of the input and output control unit 6. Explanation of the same points as in the first embodiment will be omitted.

Figure 10:
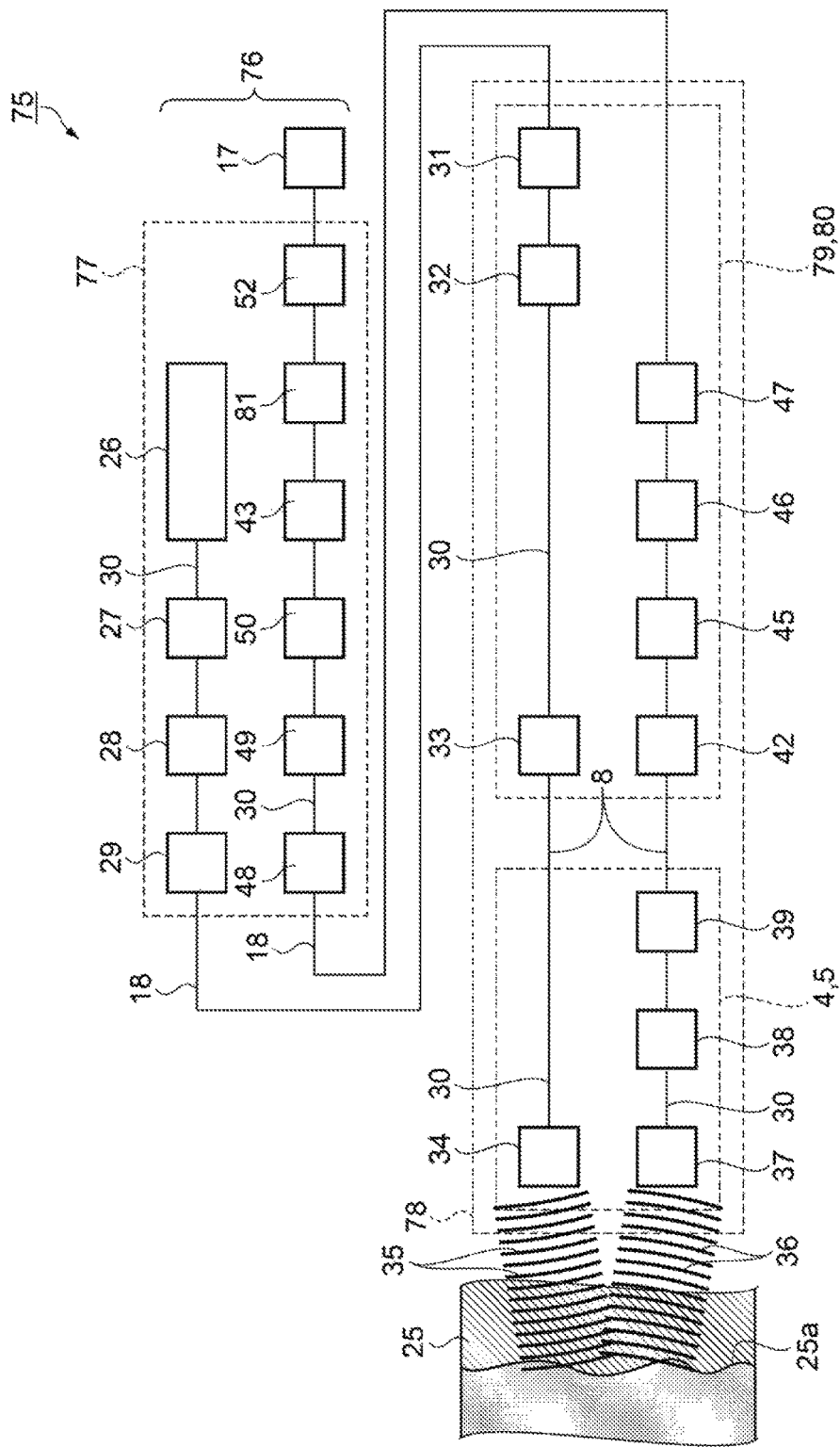
FIG. 10 is an electric block diagram of an ultrasonic measurement apparatus according to a second embodiment.

That is, in the present embodiment, as shown in FIG. 10, in an ultrasonic measurement apparatus 75, a control unit 77 is provided in a control device 76. An input and output control unit 79 is provided inside an ultrasonic probe 78, and a second circuit board 80 is provided in the input and output control unit 79. The first circuit board 5 and the second circuit board 80 are provided in the ultrasonic probe 78.

An A/D conversion unit 42, a serial conversion unit 45, a second electro-optical conversion unit 46, and a second light emitting unit 47 are provided on the second circuit board 80 of the input and output control unit 79, and these are connected to each other by the wiring 30 in this order. A second light receiving unit 48, a second photoelectric conversion unit 49, a parallel conversion unit 50, a demultiplexing processing unit 43, a phasing addition circuit 81, and an image processing unit 52 are provided in the control unit 77, and these are connected to each other by the wiring 30 in this order.

The phasing addition circuit 81 has functions of both the first phasing addition circuit 44 and the second phasing addition circuit 51 in the first embodiment. The phasing addition circuit 81 has a function of calculating a first composite signal by combining the electric signals output from the reception ultrasonic elements 37 in each row. The phasing addition circuit 81 also has a function of calculating a second composite signal by combining the first composite signals of the respective rows.

Next, the flow of the signal after the reception ultrasonic element 37 receives the reflected wave 36 will be described. The reflected wave 36 reaches a plurality of reception ultrasonic elements 37, and the plurality of reception ultrasonic elements 37 respond to the reflected wave 36. Then, the plurality of reception ultrasonic elements 37 output the ultrasonic signal corresponding to the reflected wave 36 to the multiplexing processing unit 38.

The multiplexing processing unit 38 receives the electric signals output from the plurality of ultrasonic elements, time-division multiplexes the plurality of electric signals, and outputs a multiplexed signal obtained by the time-division multiplexing to the amplification unit 39. The amplification unit 39 amplifies the multiplexed signal, and outputs the amplified multiplexed signal to the second circuit board 80 of the input and output control unit 79 through the wiring 8. On the second circuit board 80, the A/D conversion unit 42 receives the multiplexed signal.

The electric signal output from the reception ultrasonic element 37 is an analog signal, and the multiplexed signal output from the multiplexing processing unit 38 is an analog signal. Accordingly, the multiplexed signal input to the A/D conversion unit 42 is an analog signal. Then, the A/D conversion unit 42 converts the analog signal into a digital signal, and outputs the digital signal to the serial conversion unit 45. The serial conversion unit 45 receives and serializes the digital parallel signal, and outputs a serial signal to the second electro-optical conversion unit 46.

The second electro-optical conversion unit 46 and the second light emitting unit 47 receive the serial signal of the multiplexed signal, convert the serial signal of the multiplexed signal into an optical signal, and output the optical signal. In this manner, after the multiplexing processing unit 38 outputs the multiplexed signal, the second electro-optical conversion unit 46 and the second light emitting unit 47 output the optical signal. The output optical signal is transmitted to the control unit 77 of the control device 76 through the optical cable 18.

The optical signal transmitted through the optical cable 18 is a multiplexed signal obtained by time-division multiplexing of the multiplexing processing unit 38. The optical signal transmitted through the optical cable 18 is a serial signal obtained by serialization of the serial conversion unit 45. The second light receiving unit 48 and the second photoelectric conversion unit 49 receive the optical signal, and convert the optical signal into an electric signal. The electric signal is a digital serial signal.

By adopting the configuration of the present embodiment as described above, the following effect is obtained.

(1) According to the present embodiment, the ultrasonic measurement apparatus 75 includes the multiplexing processing unit 38, the second electro-optical conversion unit 46, the second light emitting unit 47, the optical cable 18, the second light receiving unit 48, and the second photoelectric conversion unit 49. The multiplexing processing unit 38 receives the electric signals output from the plurality of reception ultrasonic elements 37. Then, the multiplexing processing unit 38 time-division multiplexes the electric signals. Then, a multiplexed signal obtained by the time-division multiplexing is output. The second electro-optical conversion unit 46 and the second light emitting unit 47 receive the multiplexed signal. Then, the multiplexed signal is converted into an optical signal. The optical signal is transmitted through the optical cable 18. The second light receiving unit 48 and the second photoelectric conversion unit 49 receive the optical signal, and convert the optical signal into the multiplexed signal of the electric signal.

Since each of the reception ultrasonic elements 37 outputs an electric signal, the number of electric signals output from the group of the reception ultrasonic elements 37 increases as the number of reception ultrasonic elements 37 increases. Then, the multiplexing processing unit 38 time-division multiplexes the plurality of electric signals. In this manner, it is possible to reduce the amount of electric signals transmitted through the optical cable 18. After the multiplexing processing unit 38 outputs the multiplexed signal, the second electro-optical conversion unit 46 and the second light emitting unit 47 convert the multiplexed signal into an optical signal, and transmit the optical signal through the optical cable 18. The second light receiving unit 48 and the second photoelectric conversion unit 49 receive the optical signal, and convert the optical signal into an electric signal. The electric signal is a multiplexed signal. In this manner, it is possible to utilize the multiplexed signal output from each reception ultrasonic element 37.

When the electric signal output from the reception ultrasonic element 37 is transmitted as it is, the number of wirings for transmission is increased. For the wiring of the electric signal, metal is used. Therefore, if the number of wirings is large, it is difficult for the wirings to bend. For this reason, the operability is lowered. In the ultrasonic measurement apparatus 75 of the present embodiment, the optical signal, instead of the electric signal, is transmitted through the optical cable 18. Since a thin wire, such as a glass wire or a transparent resin wire, can be used for the optical cable 18, the optical cable 18 can be made thin so as to be able to bend. Since the multiplexing processing unit 38 is disposed between the reception ultrasonic element 37 and the second electro-optical conversion unit 46 and the second light emitting unit 47 and the multiplexing processing unit 38 time-division multiplexes the electric signal, it is possible to reduce the amount of optical signals to be transmitted. As a result, since the optical cable 18 can be made thin so as to be able to bend, the ultrasonic measurement apparatus 75 having good operability can be obtained.

(2) According to the present embodiment, the electric signal output from the reception ultrasonic element 37 is an analog signal. The ultrasonic measurement apparatus 75 includes the A/D conversion unit 42 and the serial conversion unit 45. The A/D conversion unit 42 converts the analog signal into a digital signal. By using a digital arithmetic device, an advanced calculation is performed on the digital signal. As a result, it is possible to form an ultrasonic cross-sectional image. Then, the serial conversion unit 45 serializes the digital signal to output a serial signal. Due to the serial signal, it is possible to reduce the number of signal wirings compared with a case of the parallel signal. As a result, since the optical cable 18 can be made thin so as to be able to bend, the ultrasonic measurement apparatus 75 having good operability can be obtained.

Third Embodiment

Next, an embodiment of the ultrasonic measurement apparatus will be described with reference to a block diagram showing circuits on a first circuit board and a second circuit board in FIG. 11. The present embodiment is different from the first embodiment in that the amplification unit 39 amplifies the electric signal output from the reception ultrasonic element 37 and the multiplexing processing unit 38 time-division multiplexes the electric signal. Explanation of the same points as in the first embodiment will be omitted.

Figure 11:
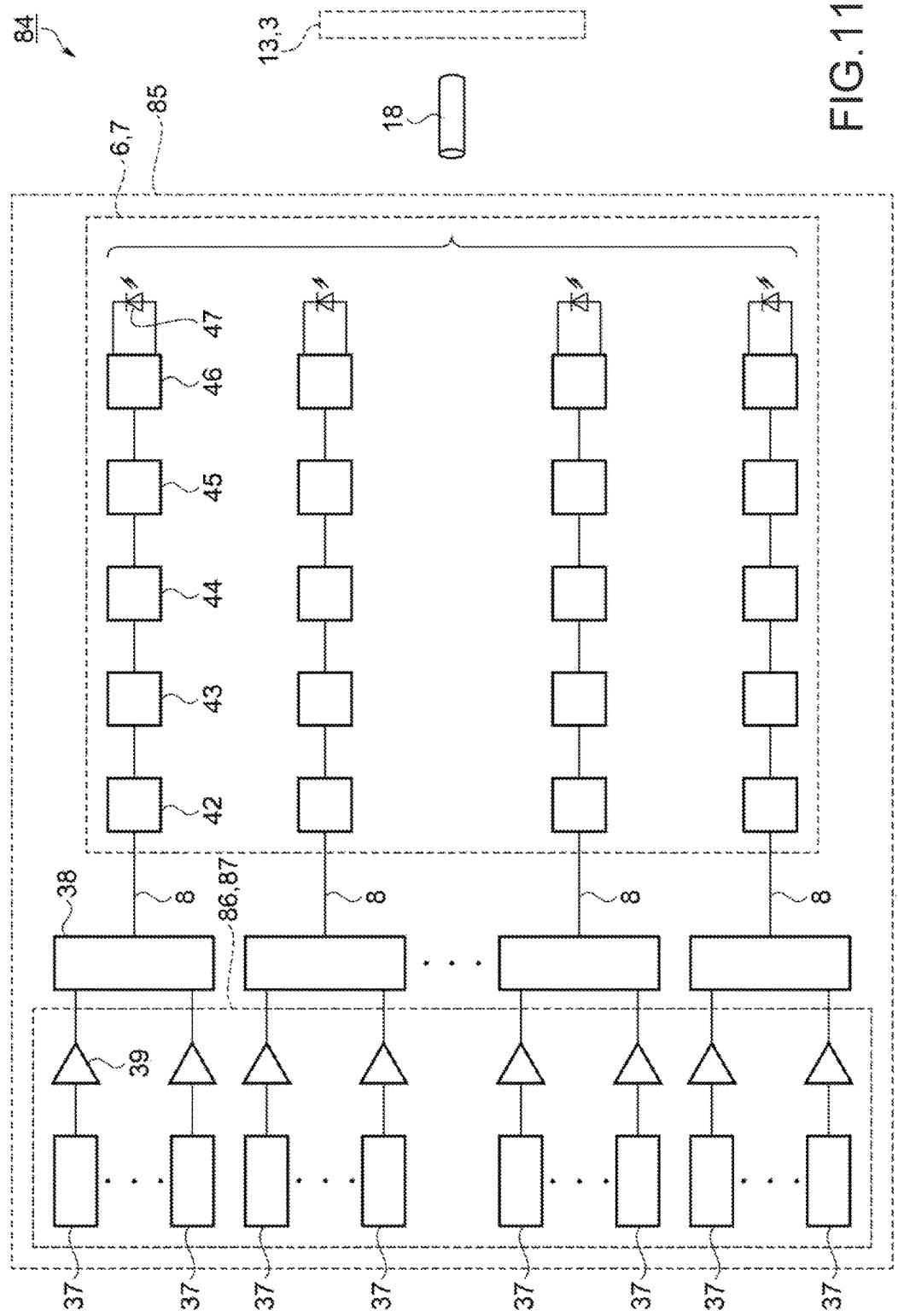
FIG. 11 is a block diagram showing circuits on a first circuit board and a second circuit board according to a third embodiment.

That is, in the present embodiment, as shown in FIG. 11, in an ultrasonic measurement apparatus 84, an ultrasonic transducer device 86 is provided in an ultrasonic probe 85, and a first circuit board 87 is provided in the ultrasonic transducer device 86. The reception ultrasonic elements 37 are arranged in a matrix in the ultrasonic transducer device 86, and each reception ultrasonic element 37 receives the reflected wave 36. Then, the waveform of the reflected wave 36 is converted into an electric signal, and the electric signal is output.

The amplification unit 39 is provided so as to be connected to the reception ultrasonic element 37, and the amplification unit 39 amplifies the electric signal output from the reception ultrasonic element 37. A plurality of amplification units 39 are connected to the multiplexing processing unit 38. The electric signal amplified by the amplification unit 39 is output to the multiplexing processing unit 38.

A larger number of amplification units 39 than in the ultrasonic transducer device 4 in the first embodiment are provided. Since the amplification unit 39 individually amplifies the output of each reception ultrasonic element 37, it is possible to improve the reception sensitivity even when the element capacity of the reception ultrasonic element 37 is small. Therefore, it is possible to improve the reception characteristic of the ultrasonic transducer device 86.

On the first circuit board 87, the amplification unit 39 is disposed adjacent to the reception ultrasonic element 37. As a result, it is possible to reduce the wiring capacity between the amplification unit 39 and the reception ultrasonic elements 37. The signal-noise ratio (S/N ratio) performance of the output of the amplification unit 39 can be improved. Therefore, even if the element capacity of the reception ultrasonic element 37 is reduced, the reception sensitivity of the reception ultrasonic element 37 can be improved.

The invention is not limited to the embodiments described above, and various modifications or improvements can be made within the technical idea of the invention by those skilled in the art. Modification examples thereof will be described below.

Modification Example 1

In the first embodiment described above, the transmission ultrasonic elements 34 arranged in a matrix emit the ultrasonic waves 35 so that the ultrasonic waves 35 converge on one point of the convergence point 62. Alternatively, the transmission ultrasonic elements 34 arranged in a matrix may emit the ultrasonic waves 35 so that the ultrasonic waves 35 linearly converge. Also in this case, the first phasing addition circuit 44 combines row composite reflected signals in each row. The image processing unit 52 may analyze the reflection strength of the reflected wave 36 at each position in the column direction of the ultrasonic transducer device 4.

Modification Example 2

In the first embodiment described above, the first heat dissipation unit 9, the second heat dissipation unit 10, and the cooling unit 14 cool the first circuit board 5 and the second circuit board 7. Alternatively, the first circuit board 5 and the second circuit board 7 may be cooled using a Peltier element. The control device 3 can be made small.

In the first embodiment described above, the pulse signal output unit 33 is provided on the second circuit board 7. When the drive voltage of the transmission ultrasonic element 34 is a low voltage and the heat generation of the pulse signal output unit 33 is small, the pulse signal output unit 33 may be provided on the first circuit board 5. Since the wiring between the pulse signal output unit 33 and the transmission ultrasonic element 34 can be shortened, it is possible to suppress the generation of electromagnetic noise.

Modification Example 3

In the first and second embodiments described above, the transmission ultrasonic element 34 emits the ultrasonic wave 35, and the reception ultrasonic element 37 receives the reflected wave 36. One ultrasonic element may have a function of emitting the ultrasonic wave 35 and a function of receiving the reflected wave 36. In this case, such an ultrasonic element can be realized by providing a switch for switching between transmission and reception on the first circuit board 5. In this case, since the density of ultrasonic elements can be increased, it is possible to increase the spatial resolution detected by the ultrasonic probe 2.

The entire disclosure of Japanese Patent Application No. 2016-168967 filed Aug. 31, 2016 is expressly incorporated by reference herein.

What is claimed is:

1. An ultrasonic measurement apparatus, comprising:
a combining processing circuit that receives electric signals output from a plurality of ultrasonic elements, shifts the plurality of electric signals in a time axis direction to combine the plurality of electric signals, and outputs a composite signal;
an electro-optical conversion unit that receives the composite signal, converts the composite signal into an optical signal, and outputs the optical signal;
an optical fiber through which the optical signal is transmitted; and
a photoelectric conversion unit that receives the optical signal and converts the optical signal into an electric signal,
wherein the electro-optical conversion unit outputs the optical signal after the combining processing circuit outputs the composite signal.

2. The ultrasonic measurement apparatus according to claim 1,
wherein the electric signal output from each of the ultrasonic elements is an analog signal,
an A/D conversion unit, which converts the analog signal into a digital signal and outputs the digital signal, and a serial conversion unit, which serializes the digital signal to output a serial signal, are provided,
the combining processing circuit outputs the composite signal after the A/D conversion unit outputs the digital signal, and
the serial conversion unit outputs the serial signal after the combining processing circuit outputs the composite signal.

3. An ultrasonic measurement apparatus, comprising:
a multiplexing processing unit that receives electric signals output from a plurality of ultrasonic elements, time-division multiplexes the plurality of electric signals, and outputs a multiplexed signal obtained by the time-division multiplexing;
an electro-optical conversion unit that receives the multiplexed signal and converts the multiplexed signal into an optical signal;
an optical fiber through which the optical signal is transmitted; and a photoelectric conversion unit that receives the optical signal and converts the optical signal into an electric signal, wherein the electro-optical conversion unit outputs the optical signal after the multiplexing processing unit outputs the multiplexed signal.

4. The ultrasonic measurement apparatus according to claim 3, wherein the electric signal output from each of the ultrasonic elements is an analog signal, and an A/D conversion unit, which converts the analog signal into a digital signal, and a serial conversion unit, which serializes the digital signal to output a serial signal, are provided.

5. The ultrasonic measurement apparatus according to claim 2, further comprising:

a first circuit board on which the plurality of ultrasonic elements are provided; and a second circuit board connected to the first circuit board by a wiring portion, wherein the A/D conversion unit is provided on the second circuit board.

6. The ultrasonic measurement apparatus according to claim 5, wherein a second heat dissipation unit that dissipates heat of the second circuit board is provided on the second circuit board.

7. The ultrasonic measurement apparatus according to claim 5, wherein a first heat dissipation unit that dissipates heat of the first circuit board is provided on the first circuit board.

8. The ultrasonic measurement apparatus according to claim 5, wherein a heat insulation unit that blocks conductive heat is provided between the first circuit board and the second circuit board.

9. The ultrasonic measurement apparatus according to claim 2, further comprising:

a multiplexing processing unit that receives the electric signals output from the plurality of ultrasonic elements, time-division multiplexes the plurality of electric signals, and outputs a multiplexed signal obtained by the time-division multiplexing;

a first circuit board on which the plurality of ultrasonic elements are provided; and a second circuit board connected to the first circuit board by a wiring portion, wherein the multiplexing processing unit is provided on the first circuit board, and the A/D conversion unit is provided on the second circuit board.

10. An ultrasonic probe, comprising:

a combining processing circuit that receives electric signals output from a plurality of ultrasonic elements, shifts the plurality of electric signals in a time axis direction to combine the plurality of electric signals, and outputs a composite signal; and an electro-optical conversion unit that receives the composite signal and converts the composite signal into an optical signal transmitted through an optical fiber, wherein the electro-optical conversion unit outputs the optical signal after the combining processing circuit outputs the composite signal.

* * * * *